(12) United States Patent
Suzuki et al.

(10) Patent No.: US 7,531,668 B2
(45) Date of Patent: May 12, 2009

(54) 2-ARYLCARBOXAMIDE-NITROGENOUS HETEROCYCLE COMPOUND

(75) Inventors: Takao Suzuki, Tsukuba (JP); Minoru Moriya, Tsukuba (JP); Shunji Sakuraba, Tsukuba (JP); Sayaka Mizutani, Tsuchiura (JP); Hisashi Iwaasa, Tsukuba (JP); Akio Kanatani, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 110 days.

(21) Appl. No.: 11/663,038

(22) PCT Filed: Sep. 30, 2005

(86) PCT No.: PCT/JP2005/018581

§ 371 (c)(1),
(2), (4) Date: Mar. 15, 2007

(87) PCT Pub. No.: WO2006/038680

PCT Pub. Date: Apr. 13, 2006

(65) Prior Publication Data

US 2007/0299070 A1  Dec. 27, 2007

(30) Foreign Application Priority Data

Oct. 1, 2004  (JP) .............................. 2004-289825

(51) Int. Cl.
C07D 235/12 (2006.01)
C07D 209/12 (2006.01)
C07D 211/06 (2006.01)
C07D 401/12 (2006.01)
C07D 291/04 (2006.01)
C07D 291/06 (2006.01)
C07D 279/02 (2006.01)
C07D 279/06 (2006.01)
C07D 279/12 (2006.01)
C07D 265/02 (2006.01)
C07D 265/06 (2006.01)
C07D 265/30 (2006.01)
C07D 257/04 (2006.01)
C07D 257/08 (2006.01)
C07D 251/04 (2006.01)
C07D 237/04 (2006.01)

(52) U.S. Cl. .................... 548/304.7; 548/492; 546/199; 546/201; 544/2; 544/13; 544/63; 544/179; 544/224

(58) Field of Classification Search .............. 548/304.7, 548/492
See application file for complete search history.

(56) References Cited

U.S. PATENT DOCUMENTS

| 6,627,651 | B1 | 9/2003 | Shiraishi et al. |
| 6,930,185 | B2 | 8/2005 | Ishihara et al. |
| 7,115,750 | B1 | 10/2006 | Kato et al. |
| 2004/0077628 | A1 | 4/2004 | Ishihara et al. |
| 2004/0220191 | A1 | 11/2004 | Schwink et al. |
| 2005/0137190 | A1* | 6/2005 | Gonzalez et al. ......... 514/225.8 |

FOREIGN PATENT DOCUMENTS

| JP | 2002-003370 | 1/2002 |
| JP | 2002/241274 | 8/2002 |
| WO | WO 00/68203 | 11/2000 |
| WO | WO 01/21577 | 3/2001 |
| WO | WO 01/82925 | 11/2001 |
| WO | WO 2004/072025 | 8/2004 |
| WO | WO 2005/004863 | * 1/2005 |
| WO | WO 2006/066173 | 6/2006 |
| WO | WO 2006/066174 | 6/2006 |

OTHER PUBLICATIONS

H. J. Dyke et al., "Recent developments in the discovery of MCH-1R antagonists for the treatment of obesity—an update", Expert Opinion Ther. Patents, vol. 15, No. 10, pp. 1303-1313 (2005).

* cited by examiner

Primary Examiner—Rebecca L Anderson
Assistant Examiner—Shawquia Young
(74) Attorney, Agent, or Firm—Janet E. Fair; Catherine D. Fitch

(57) ABSTRACT

A compound represented by the formula [I]:

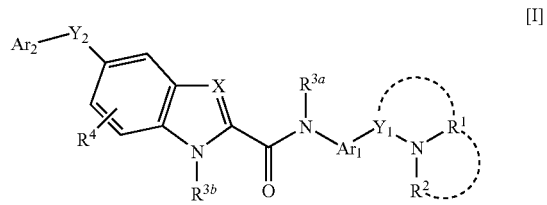

[wherein $R^1$ and $R^2$ are the same or different and each represents $C_{1-6}$ alkyl, $C_{3-8}$ cycloalkyl, et al; $R^{3a}$, $R^{3b}$, and $R^4$ are the same or different and each represents hydrogen, $C_{1-6}$ alkyl, et al; X represents —N—, —CH—, et al; $Y_1$ represents a single bond, $C_{1-3}$ alkylene, et al; $Y_2$ represents $C_{1-4}$ alkylene, oxy ($C_{1-4}$ alkylene), et al; $Ar_1$ represents a monocyclic aromatic carbocyclic group, monocyclic aromatic heterocyclic group, et al; and $Ar_2$ represents a 5- or 6-membered aromatic carbocyclic group, aromatic heterocyclic group, et al]. This compound functions as a melanin-concentrating hormone receptor antagonist and is useful as, e.g., a therapeutic agent for obesity, et al.

17 Claims, No Drawings

2-ARYLCARBOXAMIDE-NITROGENOUS HETEROCYCLE COMPOUND

CROSS-REFERENCE TO RELATED APPLICATIONS

This application is a U.S. National Phase application under 35 U.S.C. §371 of PCT Application No. PCT/JP2005/018581, filed Sep. 30, 2005, which claims priority under 35 U.S.C. §365(b) from Japanese patent application No. JP2004-289825, filed Oct. 1, 2004.

TECHNICAL FIELD

The present invention relates to 2-arylcarboxamide-nitrogenous heterocyclic compounds useful in the field of medicines. The compounds act as a melanin concentrating hormone receptor antagonist, and are useful as preventing or treating agents for various circular system diseases, nervous system diseases, metabolic diseases, reproductive diseases, respiratory diseases, digestive diseases, et al.

BACKGROUND ART

Melanin concentrating hormone (hereafter abbreviated as "MCH") is a cyclic peptide hormone/neuro-peptide, which was for the first time isolated by Kawauchi, et al., in 1983 from sermon hypophysis [Nature, Vol. 305, 321 (1983)]. The hormone is known to functionally antagonize for melanin cell stimulating hormone in fishes, to cause concentration of melanin granules in melanophore and participate in body color change [International Review of Cytology, Vol. 126, 1 (1991); Trends in Endocrinology and Metabolism, Vol. 5, 120 (1994)]. Also in mammals, MCH-containing neuron cells are localized in the hypothalamus lateral field and uncertain zone, but their nerve fibers are projecting over a very wide scope in the brain [The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being much accumulated. That is, it has been reported that expression of mRNA, which is an MCH precursor, was accelerated in the brains of ob/ob mice, db/db mice, $A^y$/a mice and Zucker fatty rats which are model animals of hereditary obesity, and in the brains of fasted mice [Nature, Vol. 380, 243 (1996); Diabetes, Vol. 47, 294 (1998); Biochemical and Biophysical Research Communications, Vol. 268, 88 (2000); Molecular Brain Research, Vol. 92, 43 (2001)].

Acute ventricular administration of MCH to rats was observed to induce accelerated feeding activity [Nature, Vol. 380, 243 (1996)] and chronic administration invites obesity accompanied by polyphagy [Proceedings of the National Academy of Sciences of the United States of America, Vol. 99, 3240 (2002)]. Moreover, MCH precursor gene-deficient mice show reduced food ingestion or rise in oxygen consumption per body weight compared to wild type mice. Their low body weight due to decrease in body fat was observed [Nature, Vol. 396, 670 (1998)].

On the contrary, transgenic mice which express excessive MCH precursor develop obesity accompanied by polyphagy and insulin resistance [The Journal of Clinical Investigation, Vol. 107, 379 (2001)]. Consequently, it is suggested that MCH is an important factor for developing obesity and participates in diseases induced by metabolic disorders or respiratory diseases of which one of risk factors is obesity. Besides, MCH is known to participate also in anxiety-causing action, epilepsy, memory, learning, diuretic action, excretory action of sodium and potassium, oxytocin secreting action, reproduction and reproductive function [Peptides, Vol. 17, 171 (1996); Peptides, Vol. 18, 1095 (1997); Peptides, Vol. 15, 757 (1994); Journal of Neuroendocrinology, Vol. 8, 57 (1996); Critical Reviews in Neurobiology, Vol. 8, 221 (1994)].

MCH causes versatile pharmacological actions through MCH receptors which are present mainly in the central nervous system. As receptors of MCH, at least two types of receptors, type 1 receptors (MCH-1R or SLC-1) and type 2 receptors (MCH-2R or SLT) are known [Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Biophysical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); Molecular Pharmacology, Vol. 60, 632 (2001)].

Of those, the pharmacological action observed on rodents is induced mainly via MCH-1R [Genomics, Vol.79, 785 (2002)]. Because MCH-1R gene-deficient mice chronically administered with MCH do not develop polyphagy or obesity, it is known that controlling of energy metabolism by MCH is induced via MCH-1R. Furthermore, the deficiency of MCH-1R is known to promote the activity amount of mice [Proceedings of the National Academy of Sciences of the United States of America, Vol. 99, 3240 (2002)], and its participation in central diseases accompanied by behavioral disorders, for example, attention-deficit hyperactivity disorder, schizophrenia, depression and the like also is strongly suggested [Molecular Medicine Today, Vol. 6, 43 (2000); Trends in Neuroscience, Vol. 24, 527 (2001)].

It is also reported that an autoantibody to MCH-1R is present in serum of vitiligo vulgaris patients [The Journal of Clinical Investigation, Vol. 109, 923 (2002)]. Furthermore, expression of MCH-1R in certain species of cancer cells was reported, and in vivo expression sites of MCH and MCH-1R also suggest MCH's participation in cancer, sleep, vigil, drug dependence and digestive disorders [Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon it binding to MCH receptors. Therefore, when the binding to MCH receptor is inhibited, then expression of MCH action can be inhibited. In consequence, substances which are antagonists for binding of MCH with its receptor are useful as preventing or treating agents of those various diseases in which MCH participates, for example, metabolic disorders represented by obesity, diabetes, hormone disorder, hyperlipidemia, gout, fatty liver, hepatitis, cirrhosis; cardiovascular disorders represented by stenocardia, acute or congestive heart failure, myocardial infarction, coronary atherosclerosis, hypertension, renal diseases, electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders represented by infertility, preterm labor and sexual dysfunction; and other digestive disorders, respiratory disorders, cancer or pigmentation.

Compounds similar to the compounds of the invention are described in WO00/68203. In this, compounds in a broad range are disclosed, but the description of the publication does not disclose concrete combinations of various substituents in the compounds of the invention. Regarding their applications, the disclosed compounds have a CCR-antagonistic effect and are useful especially for HIV-infectious diseases, and they have no relation to the present invention.

On the other hand, known melanin concentrating hormone receptor antagonists are described, for example, in WO01/21577 and WO01/82925. In particular, WO01/82925 discloses the following compounds as a melanin concentrating hormone receptor antagonist.

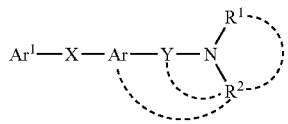

In this reference, Ar represents a condensed polycyclic aromatic ring; but $Ar_1$ in the compounds of the present invention represents a monocyclic aromatic ring. In addition, the part corresponding to $Ar_1$ in the reference significantly differs from that in the compounds of the present invention, and therefore, the compounds of the present invention differ from those in the reference. Moreover, even those skilled in the art who have seen WO01/82925 could not readily reach the knowledge that the compounds of the present invention would have an excellent effect as a melanin concentrating hormone receptor antagonist.

Patent Reference 1 WO00/68203
Patent Reference 2 WO01/21577
Patent Reference 3 WO01/82925

This invention is to provide 2-arylcarboxamide-nitrogenous heterocyclic compounds having an antagonistic effect for the binding of MCH to MCH-1R, and to provide preventing or treating agents comprising the compound for MCH-1R-related disorders of metabolic disorders, cardiovascular disorders, central nervous system or peripheral nervous system disorders, reproductive disorders, et al.

DISCLOSURE OF THE INVENTION

We, the present inventors have assiduously studied for developing compounds capable of inhibiting the binding of MCH to MCH-1R, and have found that 2-arylcarboxamide-nitrogenous heterocyclic compounds which are characterized by having a specific substituent at the 2- and 6-positions of an imidazole or indole skeleton are novel substances not described in literature, and that the compounds are effective as an MCH-1R antagonist, and on the basis of these findings, we have completed the present invention.

Specifically, the invention provides the following:

(1) A 2-arylcarboxamide-nitrogenous heterocyclic compound of the following formula [I] or pharmaceutically-acceptable salts thereof:

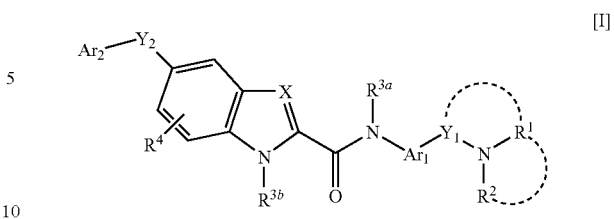

[wherein,
$R^1$ and $R^2$ are the same or different, and each represents a substituent selected from a group consisting of:
1) a $C_{1-6}$ alkyl group optionally substituted with $R^5$,
2) a $C_{3-8}$ cycloalkyl group optionally substituted with $R^6$, and
3) a 3- to 8-membered heterocycloalkyl group optionally substituted with $R^6$, or $R^1$ and $R^2$, together with the nitrogen atom to which they bond, form a 3- to 8-membered aliphatic nitrogenous heterocyclic group optionally substituted with $R^6$, or $R^1$ may form, together with the nitrogen atom adjacent to $R^1$ and $Y_1$, a 5- or 6-membered aliphatic nitrogenous heterocyclic group optionally substituted with $R^6$;

$R^{3a}$ and $R^{3b}$ are the same or different, and each represents a hydrogen atom or a $C_{1-6}$ alkyl group optionally substituted with $R^5$;

$R^4$ represents a hydrogen atom, a halogen atom, a $C_{1-6}$ alkyl group optionally substituted with $R^5$, or a $C_{1-6}$ alkyloxy group optionally substituted with $R^5$;

$R^5$ represents a substituent selected from a group consisting of a hydrogen atom, a halogen atom, a cyano group, a hydroxyl group, an amino group, a $C_{1-6}$ alkyl group optionally substituted with a fluorine atom or a hydroxyl group, a mono-$C_{1-6}$ alkylamino group, a di-$C_{1-6}$ alkylamino group, a $C_{1-6}$ alkyloxy group optionally substituted with a fluorine atom, a $C_{1-6}$ alkyloxy-$C_{1-6}$ alkyl group, a $C_{1-6}$ alkyloxycarbonyl group, a $C_{1-6}$ alkyloxycarbonylamino group, a $C_{1-6}$ alkyloxycarbonyl($C_{1-6}$ alkyl)amino group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl($C_{1-6}$ alkyl)amino group, a carbamoyl group, a mono-$C_{1-6}$ alkylcarbamoyl group, a di-$C_{1-6}$ alkylcarbamoyl group, a carbamoylamino group, a mono-$C_{1-6}$ alkylcarbamoylamino group, a di-$C_{1-6}$ alkylcarbamoylamino group, a mono-$C_{1-6}$ alkylcarbamoyl($C_{1-6}$ alkyl)amino group, a di-$C_{1-6}$ alkylcarbamoyl($C_{1-6}$ alkyl)amino group, a carbamoyloxy group, a mono-$C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, a $C_{1-6}$ alkylsulfonyl($C_{1-6}$ alkyl)amino group, a sulfamoyl group, a mono-$C_{1-6}$ alkylsulfamoyl group, a di-$C_{1-6}$ alkylsulfamoyl group, a sulfamoylamino group, a (mono-$C_{1-6}$ alkylsulfamoyl)amino group, a (di-$C_{1-6}$ alkylsulfamoyl)amino group, a mono-$C_{1-6}$ alkylsulfamoyl($C_{1-6}$ alkyl)amino group, a di-$C_{1-6}$ alkylsulfamoyl($C_{1-6}$ alkyl)amino group and a $C_{1-6}$ alkylsulfinyl group;

$R^6$ represents $R^5$ or an oxo group;

X represents —N— or —C($R^{3C}$)—, and $R^{3C}$ has the same meaning as that of $R^{3a}$;

$Y_1$ represents a single bond, a $C_{1-3}$ alkylene group or an oxy-$C_{2-3}$ alkylene group, and any hydrogen atom in the $C_{1-3}$ alkylene group or the oxy-$C_{2-3}$ alkylene group may be optionally substituted with a $C_{1-4}$ alkyl group; or $Y_1$ may form, together with the nitrogen atom adjacent to $Y_1$ and $R^1$, a 5- or 6-membered aliphatic nitrogenous heterocyclic group optionally substituted with $R^6$;

$Y_2$ represents a $C_{1-4}$ alkylene group or an oxy-$C_{1-4}$ alkylene group, and any hydrogen atom in the $C_{1-4}$ alkylene group or the oxy-$C_{1-4}$ alkylene group may be optionally substituted with a $C_{1-4}$ alkyl group;

$Ar_1$ is a divalent group, and represents a monocyclic aromatic carbocyclic group optionally substituted with $R^5$, or a monocyclic aromatic heterocyclic group optionally substituted with $R^5$;

$Ar_2$ represents a 5- or 6-membered aromatic carbocyclic group optionally substituted with $R^5$, or a 5- or 6-membered aromatic heterocyclic group optionally substituted with $R^5$].

The invention also provides the following:

(2) A method for producing a compound of formula [I], which comprises:

1) a step of condensing a compound of a formula [II]:

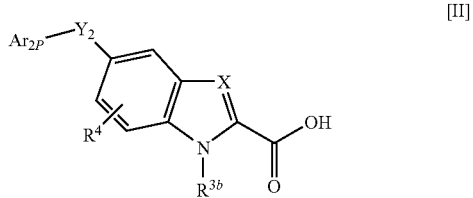

[wherein $Ar_{2P}$ represents $Ar_2$, or represents $Ar_2$ having a protective group; $R^{3b}$, $R^4$, X and $Y_2$ have the same meanings as in claim 1], with a compound of a formula [III]

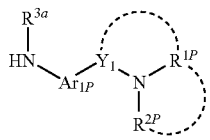

[wherein $R^{1P}$ represents $R^1$, or represents $R^1$ having a protective group; $R^{2P}$ represents $R^2$, or represents $R^2$ having a protective group; $Ar_{1P}$ represents $Ar_1$, or represents $Ar_1$ having a protective group; $R^{3a}$ and $Y_1$ have the same meanings as in claim 1] to give a compound of a formula [I-P]:

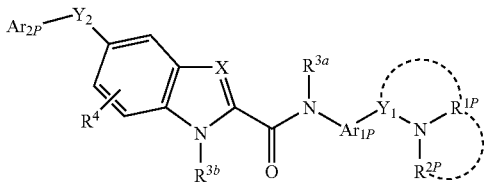

[wherein $R^{1P}$, $R^{2P}$, $Ar_{1P}$, $Ar_{2P}$, $R^{3a}$, $R^{3b}$, $R^4$, X, $Y_1$ and $Y_2$ have the same meanings as above], 2) when the compound of formula [I-P] has a protective group, a step of removing the protective group;

(3) A melanin concentrating hormone receptor antagonist comprising a compound of (1) or pharmaceutically-acceptable salts thereof as the active ingredient thereof;

(4) A pharmaceutical composition comprising a compound of (1) or pharmaceutically-acceptable salts thereof and a pharmaceutically-acceptable carrier;

(5) A preventing or treating agent comprising a compound of (1) or pharmaceutically-acceptable salts thereof as the active ingredient, for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; digestive disorders; respiratory disorders; cancer or pigmentation.

The symbols and the terms used in this description are described below.

"Halogen atom" includes a fluorine atom, a chlorine atom, a bromine atom and an iodine atom.

"$C_{1-6}$ alkyl group" means an alkyl group having from 1 to 6 carbon atoms, or that is, a linear alkyl group having from 1 to 6 carbon atoms or a branched alkyl group having from 3 to 6 carbon atoms, and concretely includes a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, a 1-ethylpropyl group, an n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, a 1-ethyl-1-methylpropyl group et al.

"$C_{3-8}$ cycloalkyl group" means a cycloalkyl group having from 3 to 8 carbon atoms, concretely including a cyclopropyl group, a cyclobutyl group, a cyclopentyl group and a cyclohexyl group, a cycloheptyl group, and a cyclooctyl group.

"Oxo group" means a group of forming a carbonyl group along with the carbon atom in organic compounds. For example, for $R^5$, it means a case where two $R^5$'s and the carbon atom bonding to them form a carbonyl group.

"$C_{1-6}$ alkyl group optionally substituted with a fluorine atom" includes a $C_{1-6}$ alkyl group, and a $C_{1-6}$ alkyl group in which a part or all of the hydrogen atoms constituting it are substituted with a fluorine atom. Concretely, the latter $C_{1-6}$ alkyl group substituted with a fluorine atom includes a fluoromethyl group, a difluoromethyl group, a trifluoromethyl group, a 1,2-difluoroethyl group et al.

"$C_{1-6}$ alkyl group optionally substituted with a hydroxyl group" includes a $C_{1-6}$ alkyl group, and a $C_{1-6}$ alkyl group in which a part or all of the hydrogen atoms constituting it are substituted with a hydroxyl group. Concretely, the latter $C_{1-6}$ alkyl group substituted with a hydroxyl group includes a hydroxymethyl group, a 2-hydroxyethyl group, a 3-hydroxypropyl group et al.

"$C_{1-6}$ alkyloxy group optionally substituted with a fluorine atom" includes a $C_{1-6}$ alkyl group or a $C_{1-6}$ alkyl group substituted with a fluorine atom, each bonding to an oxygen atom. Concretely, the $C_{1-6}$ alkyloxy group includes a methoxy group, an ethoxy group, an n-propyloxy group, an isopropyloxy group, an n-butyloxy group, an isobutoxy group, a tert-butoxy group, an n-pentyloxy group; and the $C_{1-6}$ alkyloxy group substituted with a fluorine atom includes a fluoromethoxy group, a difluoromethoxy group, a trifluoromethoxy group, a 1,2-difluoromethoxy group et al.

"Mono-$C_{1-6}$ alkylamino group" means an amino group in which one hydrogen atom is substituted with a $C_{1-6}$ alkyl group. Concretely, it includes a methylamino group, an ethylamino group, an n-propylamino group, an isopropylamino group, an n-butylamino group, a sec-butylamino group, a tert-butylamino group et al.

"Di-$C_{1-6}$ alkylamino group" means an amino group in which two hydrogen atoms are substituted with a $C_{1-6}$ alkyl group. Concretely, it includes a dimethylamino group, a diethylamino group, an ethylmethylamino group, a di-(n-propyl)amino group, a methylpropylamino group, a diisopropylamino group et al.

"$C_{1-6}$ alkyloxy-$C_{1-6}$ alkyl group" means a $C_{1-6}$ alkyl group in which one hydrogen atom is substituted with a $C_{1-6}$ alkyloxy group. Concretely, it includes a methoxymethyl group, an ethoxymethyl group, an n-propyloxymethyl group, an ethoxymethyl group, an ethoxyethyl group et al.

"$C_{1-6}$ alkyloxycarbonyl group" is a $C_{1-6}$ alkyloxy group bonding to a carbonyl group. Concretely, it includes a methoxycarbonyl group, an ethoxycarbonyl group, an n-propyloxycarbonyl group, an isopropyloxycarbonyl group, an n-butyloxycarbonyl group, an isobutoxycarbonyl group, a tert-butoxycarbonyl group, an n-pentyloxycarbonyl group et al.

"($C_{1-6}$ alkyloxycarbonyl)amino group" is a $C_{1-6}$ alkyloxycarbonyl group bonding to an amino group. Concretely, it includes a methoxycarbonylamino group, an ethoxycarbonylamino group, an n-propyloxycarbonylamino group, an isopropyloxycarbonylamino group, an n-butoxycarbonylamino group, an isobutoxycarbonylamino group, a tert-butoxycarbonylamino group, an n-pentyloxycarbonylamino group et al.

"($C_{1-6}$ alkyloxycarbonyl)$C_{1-6}$ alkylamino group" is a mono-$C_{1-6}$ alkylamino group in which the hydrogen atom on the nitrogen atom is substituted with a $C_{1-6}$ alkyloxycarbonyl group. Concretely, it includes a (methoxycarbonyl)methylamino group, an (ethoxycarbonyl)methylamino group, an (n-propyloxycarbonyl)methylamino group et al.

"$C_{1-6}$ alkylcarbonyl group" is a $C_{1-6}$ alkyl group bonding to a carbonyl group. Concretely, it includes an acetyl group, a propionyl group, a butyryl group, an isobutyryl group, a valeryl group, an isovaleryl group, a pivaloyl group et al.

"$C_{1-6}$ alkylcarbonyloxy group" is a $C_{1-6}$ alkylcarbonyl group bonding to an oxygen atom. Concretely, it includes an acetoxy group, a propionyloxy group, valeryloxy group, an isovaleryloxy group, a pivaloyloxy group et al.

"$C_{1-6}$ alkylcarbonylamino group" is an amino group in which one hydrogen atom is substituted with a $C_{1-6}$ alkylcarbonyl group. Concretely, it includes an acetamido group, an propionylamino group, an isobutyrylamino group, a valerylamino group, an isovalerylamino group, a pivaloylamino group et al.

"($C_{1-6}$ alkylcarbonyl)-$C_{1-6}$ alkylamino group" is a mono-$C_{1-6}$ alkylamino group in which the hydrogen atom on the nitrogen atom is substituted with a $C_{1-6}$ alkylcarbonyl group, including a (methylcarbonyl)methylamino group, an (ethylcarbonyl)methylamino group, an (n-propylcarbonyl)methylamino group et al.

"Mono-$C_{1-6}$ alkylcarbamoyl group" is a carbamoyl group in which one hydrogen atom is substituted with a $C_{1-6}$ alkyl group. Concretely, it includes a methylcarbamoyl group, an ethylcarbamoyl group, an n-propylcarbamoyl group, an isopropylcarbamoyl group, an n-butylcarbamoyl group, a sec-butylcarbamoyl group, a tert-butylcarbamoyl group et al.

"Di-$C_{1-6}$ alkylcarbamoyl group" is a carbamoyl group in which two hydrogen atoms are substituted with a $C_{1-6}$ alkyl group. Concretely, it includes a dimethylcarbamoyl group, a diethylcarbamoyl group, an ethylmethylcarbamoyl group, a di(n-propyl)carbamoyl group, a methylpropylcarbamoyl group, a diisopropylcarbamoyl group et al.

"Mono-$C_{1-6}$ alkylcarbamoylamino group" is an amino group in which one hydrogen atom is substituted with a $C_{1-6}$ alkylcarbamoyl group. Concretely, it includes a methylcarbamoylamino group, an ethylcarbamoylamino group, an n-propylcarbamoylamino group, an isopropylcarbamoylamino group, an n-butylcarbamoylamino group, a sec-butylcarbamoylamino group, a tert-butylcarbamoylamino group et al.

"Di-$C_{1-6}$ alkylcarbamoylamino group" is an amino group in which one hydrogen atom is substituted with a di-$C_{1-6}$ alkylcarbamoyl group. Concretely, it includes a dimethylcarbamoylamino group, a diethylcarbamoylamino group, a di(n-propyl)carbamoylamino group, a diisopropylcarbamoylamino group, a di(n-butyl)carbamoylamino group, a di(sec-butyl)carbamoylamino group, a di(tert-butyl)carbamoylamino group et al.

"Mono-$C_{1-6}$ alkylcarbamoyl($C_{1-6}$ alkyl)amino group" is a mono-$C_{1-6}$ alkylamino group in which the hydrogen atom on the nitrogen atom is substituted with a mono-$C_{1-6}$ alkylcarbamoyl group. Concretely, it includes a monomethylcarbamoyl(methyl)amino group, a monoethylcarbamoyl(methyl)amino group, a mono(n-propyl)carbamoyl(methyl)amino group et al.

"Di-$C_{1-6}$ alkylcarbamoyl($C_{1-6}$ alkyl)amino group" is a mono-$C_{1-6}$ alkylamino group in which the hydrogen atom on the nitrogen atom is substituted with a di-$C_{1-6}$ alkylcarbamoyl group. Concretely, it includes a dimethylcarbamoyl(methyl)amino group, a diethylcarbamoyl(methyl)amino group, a di(n-propyl)carbamoyl(methyl)amino group et al.

"Mono-$C_{1-6}$ alkylcarbamoyloxy group" is a $C_{1-6}$ alkylcarbamoyl group bonding to an oxygen atom. Concretely, it includes a methylcarbamoyloxy group, an ethylcarbamoyloxy group, an n-propylcarbamoyloxy group, an isopropylcarbamoyloxy group, an n-butylcarbamoyloxy group, a sec-butylcarbamoyloxy group, a tert-butylcarbamoyloxy group et al.

"Di-$C_{1-6}$ alkylcarbamoyloxy group" is a di-$C_{1-6}$ alkylcarbamoyl group bonding to an oxygen atom. Concretely, it includes a dimethylcarbamoyloxy group, a diethylcarbamoyloxy group, an ethylmethylcarbamoyloxy group, a di(n-propyl)carbamoyloxy group, a methylpropylcarbamoyloxy group, a diisopropylcarbamoyloxy group et al.

"$C_{1-6}$ alkylsulfonyl group" is a $C_{1-6}$ alkyl group bonding to a sulfonyl group, concretely including a methylsulfonyl group, an ethylsulfonyl group, an n-propylsulfonyl group, an isopropylsulfonyl group, an n-butylsulfonyl group, sec-butylsulfonyl group, a tert-butylsulfonyl group et al.

"$C_{1-6}$ alkylsulfonylamino group" is an amino group in which one hydrogen atom is substituted with a $C_{1-6}$ alkylsulfonyl group. Concretely, it includes a methylsulfonylamino group, an ethylsulfonylamino group, an n-propylsulfonylamino group, an isopropylsulfonylamino group, an n-butylsulfonylamino group, a sec-butylsulfonylamino group, a tert-butylsulfonylamino group et al.

"$C_{1-6}$ alkylsulfonyl($C_{1-6}$ alkyl)amino group" is a $C_{1-6}$ alkylamino group in which the hydrogen atom on the nitrogen atom is substituted with a $C_{1-6}$ alkylsulfonyl group. Concretely, it includes a methylsulfonyl(methyl)amino group, an ethylsulfonyl(methyl)amino group, an (n-propyl)sulfonyl(methyl)amino group et al.

"Mono-$C_{1-6}$ alkylsulfamoyl group" is a sulfamoyl group with a $C_{1-6}$ alkyl group bonding thereto. Concretely, it includes a monomethylsulfamoyl group, a monoethylsulfamoyl group, a mono(n-propyl)sulfamoyl group, a monoisopropylsulfamoyl group, a mono(n-butyl)sulfamoyl group, a mono(sec-butyl)sulfamoyl group, a mono(tert-butyl)sulfamoyl group et al.

"Di-$C_{1-6}$ alkylsulfamoyl group" is a sulfamoyl group with two $C_{1-6}$ alkyl groups bonding thereto. Concretely, it includes a dimethylsulfamoyl group, a diethylsulfamoyl group, a di(n-propyl)sulfamoyl group, a diisopropylsulfamoyl group, a di(n-butyl)sulfamoyl group, a di(sec-butyl)sulfamoyl group, a di(tert-butyl)sulfamoyl group et al.

"(Mono-$C_{1-6}$ alkylsulfamoyl)amino group" is an amino group in which one hydrogen atom is substituted with a mono-$C_{1-6}$ alkylsulfamoyl group. Concretely, it includes a (monomethylsulfamoyl)amino group, a (monoethylsulfamoyl)amino group, a [mono(n-propyl)sulfamoyl]amino group, a (monoisopropylsulfamoyl)amino group, a [mono(n-butyl)sulfamoyl]amino group, a [mono(sec-butyl)sulfamoyl] amino group, a (tert-butylsulfamoyl)amino group et al.

"(Di-$C_{1-6}$ alkylsulfamoyl)amino group" is an amino group in which one hydrogen atom is substituted with a di-$C_{1-6}$ alkylsulfamoyl group. Concretely, it includes a (dimethylsulfamoyl)amino group, a (diethylsulfamoyl)amino group, a (ethylmethylsulfamoyl)amino group, a [di(n-propyl)sulfamoyl]amino group, a (methylpropylsulfamoyl)amino group, a (diisopropylsulfamoyl)amino group et al.

"Mono-$C_{1-6}$ alkylsulfamoyl($C_{1-6}$ alkyl)amino group" is a mono-$C_{1-6}$ alkylamino group in which the hydrogen atom on the nitrogen atom is substituted with a mono-$C_{1-6}$ alkylsulfamoyl group. Concretely, it includes a monomethylsulfamoyl (methyl)amino group, a monoethylsulfamoyl(methyl)amino group, a mono(n-propyl)sulfamoyl(methyl)amino group et al.

"Di-$C_{1-6}$ alkylsulfamoyl($C_{1-6}$ alkyl)amino group" is a mono-$C_{1-6}$ alkylamino group in which the hydrogen atom on the nitrogen atom is substituted with a di-$C_{1-6}$ alkylsulfamoyl group. Concretely, it includes a dimethylsulfamoyl(methyl) amino group, a diethylsulfamoyl(methyl)amino group, a di(n-propyl)sulfamoyl(methyl)amino group et al.

"$C_{1-6}$ alkylsulfinyl group" includes a $C_{1-6}$ alkyl group bonding to a sulfur atom, concretely including a methylsulfinyl group, an ethylsulfinyl group, an n-propylsulfinyl group, an isopropylsulfinyl group, an n-butylsulfinyl group et al.

"3- to 8-Membered heterocycloalkyl group" includes an azetidinyl group, a pyrrolidinyl group, a piperidinyl group, a piperazinyl group, an imidazolidinyl group, a tetrahydrofuranyl group, a tetrahydropyranyl group, a morpholinyl group, a 1-thia-4-azocyclohexyl group, a 2,5-diazabicyclo[2.2.2]octanyl group et al.

"Pharmaceutically-acceptable salts" of a compound of formula [I] mean ordinary salts those are acceptable as medicines. Their examples are acid-addition salts to the amino group or acid-addition salts to the nitrogenous hetero ring, or base-addition salts to the acidic substituent.

The acid-addition salts include inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The base-addition salts include alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

For the purpose of more concretely disclosing the compounds of the invention hereinunder, various symbols used in formula [I] are described in detail with reference to their examples. The position numbering in the 2-arylcarboxamide-nitrogenous heterocyclic compound skeleton is as follows:

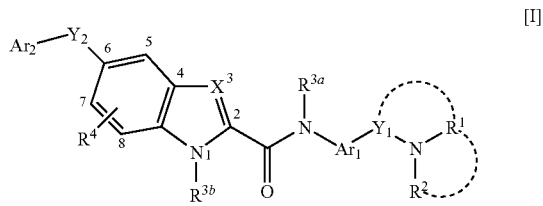

[I]

Compounds of formula [I]

In compounds of formula [I], $R^1$ and $R^2$ are the same or different, and each represents a substituent selected from a group consisting of:
1) a $C_{1-6}$ alkyl group optionally substituted with $R^5$,
2) a $C_{3-8}$ cycloalkyl group optionally substituted with $R^6$, and
3) a 3- to 8-membered heterocycloalkyl group optionally substituted with $R^6$, or $R^1$ and $R^2$, together with the nitrogen atom to which they bond, form a 3- to 8-membered aliphatic nitrogenous heterocyclic group optionally substituted with $R^6$, and $R^1$ may form, together with the nitrogen atom adjacent to $R^1$ and $Y_1$, a 5- or 6-membered aliphatic nitrogenous heterocyclic group optionally substituted with $R^6$.

$R^5$ represents a substituent selected from a group consisting of a hydrogen atom, a halogen atom, a cyano group, a hydroxyl group, an amino group, a $C_{1-6}$ alkyl group optionally substituted with a fluorine atom or a hydroxyl group, a mono-$C_{1-6}$ alkylamino group, a di-$C_{1-6}$ alkylamino group, a $C_{1-6}$ alkyloxy group optionally substituted with a fluorine atom, a $C_{1-6}$ alkyloxy-$C_{1-6}$ alkyl group, a $C_{1-6}$ alkyloxycarbonyl group, a $C_{1-6}$ alkyloxycarbonylamino group, a $C_{1-6}$ alkyloxycarbonyl($C_{1-6}$ alkyl)amino group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl($C_{1-6}$ alkyl)amino group, a carbamoyl group, a mono-$C_{1-6}$ alkylcarbamoyl group, a di-$C_{1-6}$ alkylcarbamoyl group, a carbamoylamino group, a mono-$C_{1-6}$ alkylcarbamoylamino group, a di-$C_{1-6}$ alkylcarbamoylamino group, a mono-$C_{1-6}$ alkylcarbamoyl ($C_{1-6}$ alkyl)amino group, a di-$C_{1-6}$ alkylcarbamoyl($C_{1-6}$ alkyl)amino group, a carbamoyloxy group, a mono-$C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, a $C_{1-6}$ alkylsulfonyl($C_{1-6}$ alkyl)amino group, a sulfamoyl group, a mono-$C_{1-6}$ alkylsulfamoyl group, a di-$C_{1-6}$ alkylsulfamoyl group, a sulfamoylamino group, a (mono-$C_{1-6}$ alkylsulfamoyl)amino group, a (di-$C_{1-6}$ alkylsulfamoyl)amino group, a mono-$C_{1-6}$ alkylsulfamoyl($C_{1-6}$ alkyl)amino group, a di-$C_{1-6}$ alkylsulfamoyl($C_{1-6}$ alkyl)amino group and a $C_{1-6}$ alkylsulfinyl group.

Concretely, examples of $R^5$ are a hydrogen atom; a halogen atom such as a chlorine atom, a fluorine atom et al; a $C_{1-6}$ alkyl group such as a methyl group, an ethyl group, an n-propyl group, an isopropyl group et al; a $C_{1-6}$ alkyl group substituted with a fluorine atom, such as a fluoromethyl group, a difluoromethyl group, a trifluoromethyl group et al; a $C_{1-6}$ alkyloxy group such as a methoxy group, an ethoxy group, an isopropyloxy group et al; a $C_{1-6}$ alkyloxy group substituted with a fluorine atom, such as a difluoromethoxy group, a trifluoromethoxy group et al; a $C_{1-6}$ alkylsulfonyl group such as a methylsulfonyl group, an ethylsulfonyl group et al; a $C_{3-6}$ cycloalkyl group such as a cyclopropyl group, a cyclobutyl group, a cyclopentyl group et al; a $C_{3-6}$ cycloalkyloxy group such as a cyclopropyloxy group, a cyclobutyloxy group et al; a $C_{1-6}$ alkyl group substituted with a hydroxyl group, such as a hydroxymethyl group, a 2-hydroxyethyl group, a 1-hydroxy-1-methylethyl group et al; a dialkylamino group such as a dimethylamino group, a diethylamino group et al; a $C_{1-6}$ alkylsulfinyl group such as a methylsulfinyl group, an ethylsulfinyl group et al; a methylsulfanyl group, a nitrile group. Preferably, $R^5$ is a hydrogen atom, a hydroxyl group, a methoxycarbonyl group, an ethoxycarbonyl group et al.

Examples of $R^6$ are $R^5$ or an oxo group. Preferably, $R^6$ is a hydrogen atom, a hydroxyl group, a methoxycarbonyl group, an ethoxycarbonyl group, an oxo group et al.

Concretely, examples of $R^1$ and $R^2$ are a methyl group, an ethyl group, an n-propyl group, an isopropyl group, an n-butyl group, an isobutyl group, a methoxymethyl group, a methoxyethyl group, an ethoxyethyl group, a dimethylaminoethyl group, a dimethylaminopropyl group; a cyclopentyl group, a cyclohexyl group, a cycloheptyl group; an aziridinyl group, a pyrrolidinyl group, a piperidinyl group, a piperazinyl group, a tetrahydropyranyl group, a tetrahydrofuranyl group, a morpholinyl group; a fluoroethyl group, a fluorobutyl group, a trifluoromethoxyethyl group, a trifluoromethoxybutyl group et al.

Examples of the ring of the 3- to 8-membered aliphatic nitrogenous heterocyclic group to be formed by $R^1$ and $R^2$ together with the nitrogen atom to which they bond, are aziridine, pyrrolidine, piperazine, piperidine, hexamethyleneimine, morpholine et al.

Examples of the ring of the 5- or 6-membered aliphatic nitrogenous heterocyclic group optionally substituted with $R^6$, which may be formed by $R^1$ together with the adjacent nitrogen atom and $Y_1$, are pyrrolidine and piperidine, concretely the following:

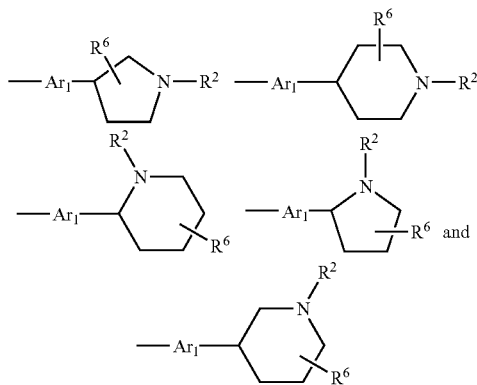

Especially preferred examples of $R^1$ and $R^2$ that are the same or different, are a methyl group, an ethyl group, an isopropyl group, a dimethylaminoethyl group, a methoxyethyl group, a cyclopropyl group, a cyclobutyl group, a cyclopentyl group, a cyclohexyl group et al.

Preferably, the aliphatic nitrogenous heterocyclic group to be formed by $R^1$ and $R^2$ is a 5- or 6-membered group, concretely including a morpholinyl group, a pyrrolidinyl group, a piperidinyl group, a piperazinyl group, a 3-fluoro-1-pyrrolidinyl group, a 3-hydroxy-1-pyrrolidinyl group, a 2-hydroxymethyl-1-pyrrolidinyl group, a 3,3-difluoro-1-pyrrolidinyl group, a 2-oxo-1-pyrrolidinyl group, a 3-oxo-1-pyrrolidinyl group, a 4-methoxy-1-piperidinyl group et al.

$R^{3a}$ and $R^{3b}$ are the same or different, and each represents a hydrogen atom or a $C_{1-6}$ alkyl group optionally substituted with $R^5$. Concretely, for example, they include a hydrogen atom, a fluorine atom, a chlorine atom, a methyl group, an ethyl group, an n-propyl group, an isopropyl group, an n-butyl group, a t-butyl group et al. Preferably, a hydrogen atom, a methyl group, an ethyl group are recommended.

$R^4$ represents a hydrogen atom, a halogen atom, a $C_{1-6}$ alkyl group optionally substituted with $R^5$, or a $C_{1-6}$ alkyloxy group optionally substituted with $R^5$. Concretely, it includes a hydrogen atom, a methyl group, an ethyl group, an n-propyl group, an isopropyl group, an n-butyl group, preferably a hydrogen atom, a methyl group are recommended.

X represents —N— or —C($R^{3C}$)—, and $R^{3C}$ has the same meaning as that of $R^{3a}$. X is preferably —N—, —CH—, —C(CH$_3$)—, —C(C$_2$H$_5$)—; more preferably —N— or —CH—.

$Y_1$ represents a single bond, a $C_{1-3}$ alkylene group or an oxy-$C_{2-3}$ alkylene group, and any hydrogen atom in the $C_{1-3}$ alkylene group or the oxy-$C_{2-3}$ alkylene group may be optionally substituted with a $C_{1-4}$ alkyl group. $Y_1$ may form, together with the nitrogen atom adjacent to $Y_1$ and $R^1$, a 5- or 6-membered aliphatic nitrogenous heterocyclic group optionally substituted with $R^6$.

Concretely, $Y_1$ includes the following:
a single bond,
—CH$_2$—,
—CH(CH$_3$)—,
—CH$_2$—CH$_2$—,
—CH$_2$—CH(CH$_3$)—,
—CH$_2$—CH$_2$—CH$_2$—,
—O—CH$_2$—CH$_2$—,
—O—CH—CH(CH$_3$)—,
—O—CH$_2$—CH$_2$—CH$_2$—.
Preferably, $Y_1$ is —CH$_2$—, —O—CH$_2$—CH$_2$—, —O—CH$_2$—CH$_2$—CH$_2$—.

$Y_2$ represents a $C_{1-4}$ alkylene group or an oxy-$C_{1-4}$ alkylene group, and any hydrogen atom in the $C_{1-4}$ alkylene group or the oxy-$C_{1-4}$ alkylene group may be optionally substituted with a $C_{1-4}$ alkyl group.

Concretely, $Y_2$ includes the following:
—CH$_2$—,
—CH$_2$CH$_2$—,
—CH$_2$CH$_2$CH$_2$—,
—CH$_2$CH$_2$CH$_2$CH$_2$—,
—CH$_2$CH(CH$_3$)—,
—CH$_2$—O—,
—CH$_2$CH$_2$—O—,
—CH$_2$CH$_2$CH$_2$—O—,
—CH$_2$CH$_2$CH$_2$CH$_2$—O—,
—CH(CH$_3$)CH$_2$—O—,
—O—CH$_2$—,
—O—CH$_2$CH$_2$—,
—O—CH$_2$CH$_2$CH$_2$—,
—O—CH$_2$CH$_2$CH$_2$CH$_2$—,
—O—CH$_2$CH$_2$CH$_2$CH(CH$_3$)—.
Preferably, $Y_2$ is —CH$_2$—, —CH$_2$CH$_2$—, —CH$_2$—O—, more preferably —CH$_2$—O—.

$Ar_1$ is a divalent group, and represents a monocyclic aromatic carbocyclic group optionally substituted with $R^5$, or a monocyclic aromatic heterocyclic group optionally substituted with $R^5$.

The aromatic carbocyclic ring or the aromatic heterocyclic ring in the "monocyclic aromatic carbocyclic group or the monocyclic aromatic heterocyclic group" is, for example, a 6-membered ring, including, benzene, pyridine, pyrazine, pyridazine, pyrimidine.

Concretely, $Ar_1$ includes the following:

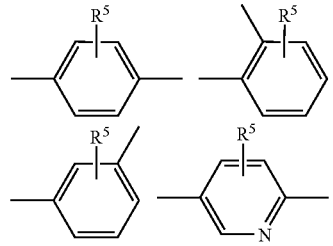

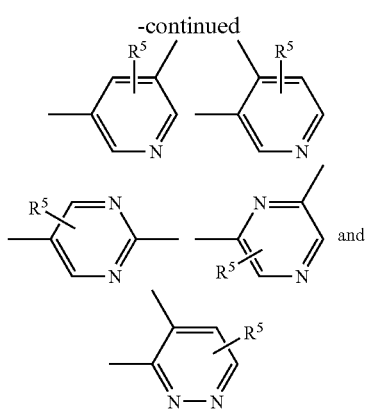

Preferably, Ar₁ includes the following:

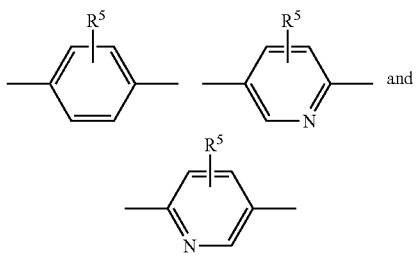

In these, $R^5$ is preferably a $C_{1-4}$ alkyl group, a $C_{1-4}$ alkyloxy group, a halogen atom et al.

Ar₂ represents a 5- or 6-membered aromatic carbocyclic group optionally substituted with $R^5$, or a 5- or 6-membered aromatic heterocyclic group optionally substituted with $R^5$.

The aromatic carbocyclic ring or the aromatic heterocyclic ring in the "monocyclic aromatic carbocyclic group or the monocyclic aromatic heterocyclic group" for Ar₂ includes, for example, benzene, pyridine, pyrimidine, pyridazine, pyrazine, pyrazole, pyrrole, imidazole, triazole, oxazole, isoxazole, oxadiazole, thiazole, isothiazole, thiadiazole, tetrazole et al.

$R^5$ with which Ar₂ may be substituted is preferably a chloro group, a fluoro group, a bromo group, a methyl group, an ethyl group, an isopropyl group, a 1-hydroxy-1-methylethyl group, a difluoromethyl group, a trifluoromethyl group, a methoxy group, an ethoxy group, an isopropyloxy group, a difluoromethoxy group, a trifluoromethoxy group, a cyclopropyl group, a cyclopropyloxy group, a methylsulfonyl group, an ethylsulfonyl group, a methylsulfanyl group, a methylsulfinyl group, a nitrile group, a dimethylamino group et al.

Concretely, Ar₂ includes a phenyl group, a 2-fluorophenyl group, a 3-fluorophenyl group, a 4-fluorophenyl group, a 4-chlorophenyl group, a 3,4-difluorophenyl group, a 2,4-difluorophenyl group, a 2-trifluoromethylphenyl group, a 3-trifluoromethylphenyl group, a 4-trifluoromethylphenyl group, a 4-methoxyphenyl group, a 4-methylsulfonylphenyl group, a 3-fluoro-4-methoxyphenyl group, 4-methanesulfinylphenyl group, a 4-methylsulfanylphenyl group, a 4-ethanesulfonylphenyl group, a pyridinyl group, a 6-fluoro-3-pyridinyl group, a 5-fluoro-2-pyridinyl group, a 5-trifluoromethyl-2-pyridinyl group, a 6-trifluoromethyl-3-pyridinyl group, a 6-chloro-3-pyridinyl group, a 5-chloro-2-pyridinyl group, a 4-bromo-2-pyridinyl group, a 6-methoxy-3-pyridinyl group, a 6-methoxy-2-pyridinyl group, a 5-methoxy-2-pyridinyl group, a 6-difluoromethoxy-3-pyridinyl group, a 5-difluoromethoxy-2-pyridinyl group, a 6-trifluoromethoxy-3-pyridinyl group, a 5-trifluoromethoxy-2-pyridinyl group, a 6-methyl-3-pyridinyl group, a 5-methyl-2-pyridinyl group, a 5-isopropyl-2-pyridinyl group, a 6-trifluoromethyl-3-pyridinyl group, a 5-trifluoromethyl-2-pyridinyl group, a 6-difluoromethyl-3-pyridinyl group, a 5-difluoromethyl-2-pyridinyl group, a 5-(1-hydroxy-1-methylethyl)-2-pyridinyl group, a 4-methanesulfonyl-2-pyridinyl group, a 4-methanesulfinyl-2-pyridinyl group, a 5-cyano-2-pyridinyl group, a 6-dimethylamino-3-pyridinyl group, a 5-cyclopropyloxy-2-pyridinyl group, a 5-isopropyloxy-2-pyridinyl group, a 4-methylsulfanyl-2-pyridinyl group, a pyrazinyl group, a 2-pyrimidinyl group, a 5-trifluoromethyl-2-pyrimidinyl group, a 3-pyridazinyl group, a 1-pyrrolyl group, a 2-imidazolyl group, a 1-imidazolyl group, a 1-triazolyl group, a 3-isoxazolyl group, a 1,3,4-oxadiazol-2-yl group, a 5-methyl-1,3,4-oxadiazol-2-yl group, a 2-thiazolyl group, a 1-thiadiazolyl group, a 1-tetrazolyl group, a cyclohexyl group et al.

Preferably, Ar₂ includes a phenyl group, a 2-fluorophenyl group, a 3-fluorophenyl group, a 4-fluorophenyl group, a 4-chlorophenyl group, a 3,4-difluorophenyl group, a 2,4-difluorophenyl group, a 2-trifluoromethylphenyl group, a 3-trifluoromethylphenyl group, a 4-trifluoromethylphenyl group, a 4-methoxyphenyl group, a 4-methanesulfonylphenyl group, a 2-pyridinyl group, a 5-methyl-2-pyridinyl group, a 6-difluoromethyl-3-pyridinyl group, a 5-difluoromethyl-2-pyridinyl group, a 6-fluoro-3-pyridinyl group, a 5-fluoro-2-pyridinyl group, a 6-chloro-3-pyridinyl group, a 5-chloro-2-pyridinyl group, a 4-chloro-2-pyridinyl group, a 6-methoxy-3-pyridinyl group, a 6-methoxy-2-pyridinyl group, a 5-methoxy-2-pyridinyl group, a 6-difluoromethoxy-3-pyridinyl group, a 5-difluoromethoxy-2-pyridinyl group, a 5-trifluoromethyl-2-pyridinyl group, a 6-trifluoromethyl-3-pyridinyl group, a 4-methylsulfanyl-2-pyridinyl group, a 2-pyrimidinyl group, a pyrazinyl group, a 3-pyridazinyl group et al; more preferably a phenyl group, a 4-fluorophenyl group, a 4-chlorophenyl group, a 4-trifluoromethylphenyl group, a 2-pyridinyl group, a 6-chloro-3-pyridinyl group, a 5-chloro-2-pyridinyl group, a 5-trifluoromethyl-2-pyridinyl group et al.

Concrete examples of the compounds of formula [I] are, for example, those in Table 1 or Table 2.

TABLE 1

Structural Formula 1-1 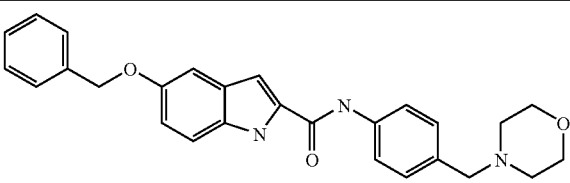

TABLE 1-continued

| | Structural Formula |
|---|---|
| 1-2 | |
| 1-3 | |
| 1-4 | |
| 1-5 | |
| 1-6 | |
| 1-7 | |
| 1-8 | |
| 1-9 | |

TABLE 1-continued
Structural Formula
1-10 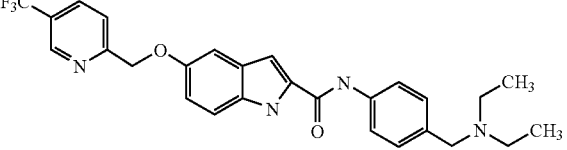
1-11 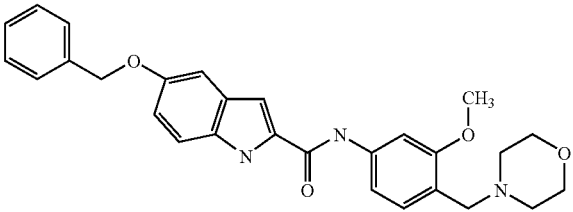
1-12 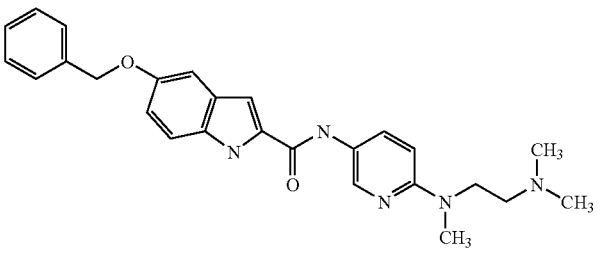
1-13 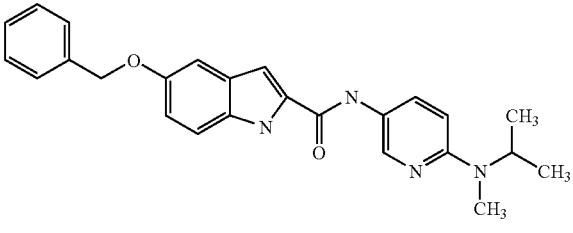
1-14 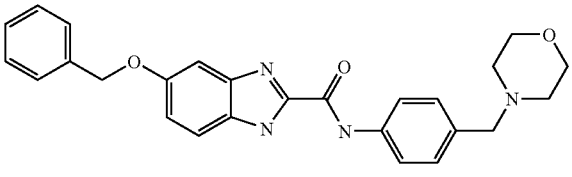
TABLE 2
Structural Formula
2-1 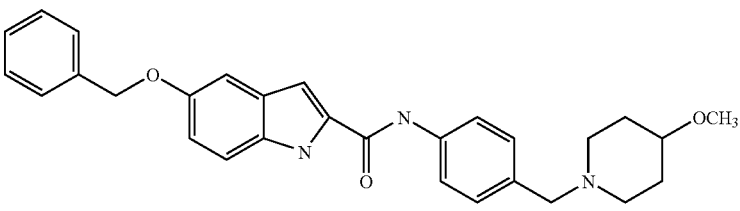

TABLE 2-continued

| | Structural Formula |
|---|---|
| 2-2 | 5-benzyloxy-indole-2-carboxylic acid [4-(dimethylaminomethyl)phenyl]amide |
| 2-3 | 5-benzyloxy-indole-2-carboxylic acid [4-(isopropylmethylaminomethyl)phenyl]amide |
| 2-4 | 5-benzyloxy-indole-2-carboxylic acid [4-(cyclohexylmethylaminomethyl)phenyl]amide |
| 2-5 | 5-benzyloxy-indole-2-carboxylic acid [4-(piperidin-1-ylmethyl)phenyl]amide |
| 2-6 | 5-benzyloxy-indole-2-carboxylic acid [4-(pyrrolidin-1-ylmethyl)phenyl]amide |
| 2-7 | 5-benzyloxy-indole-2-carboxylic acid [4-(diisopropylaminomethyl)phenyl]amide |
| 2-8 | 5-benzyloxy-indole-2-carboxylic acid [4-({ethyl-(2-methoxyethyl)amino}methyl)phenyl]amide |

TABLE 2-continued
Structural Formula
2-9 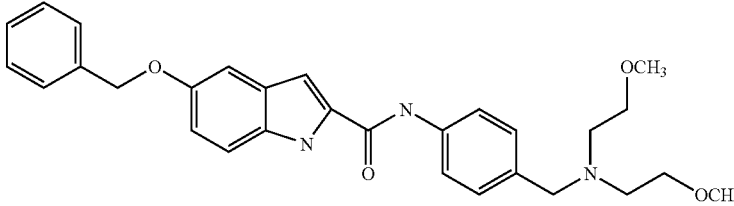
2-10 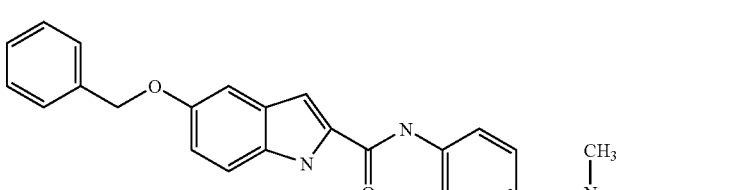
2-11 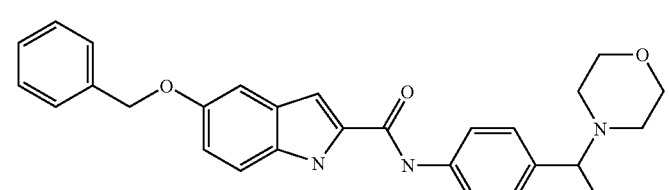
2-12 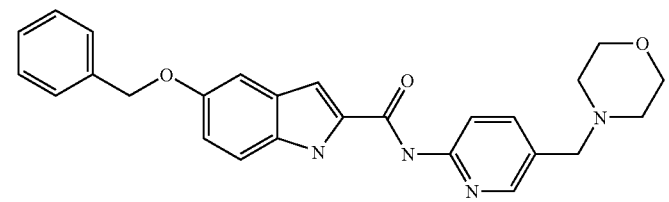
2-13 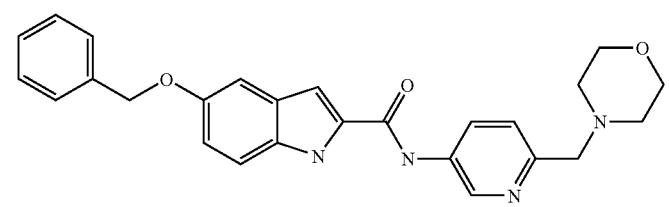
Of the compounds of formula [I], preferred are the following:
(A) Compounds of the following formula [I-A] or pharmaceutically-acceptable salts thereof:
[wherein $R^1$, $R^2$, $R^{3a}$, $R^{3b}$, $R^4$, $Y_1$ and $Ar_2$ have the same meanings as above].
(B) Compounds of the following formula [I-B] or pharmaceutically-acceptable salts thereof:
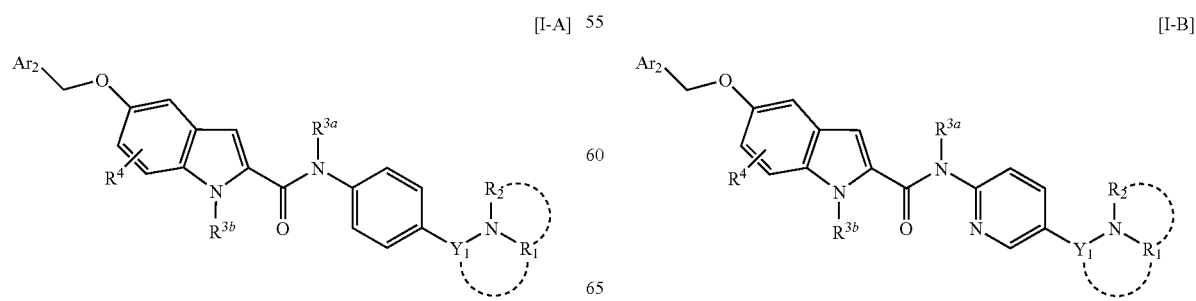

[wherein $R^1$, $R^2$, $R^{3a}$, $R^{3b}$, $R^4$, $Y_1$ and $Ar_2$ have the same meanings as above].

(C) Compounds of (A) or (B) or pharmaceutically-acceptable salts thereof, wherein $R^1$ and $R^2$ are the same or different, and each represents a group selected from a methyl group, an ethyl group, an isopropyl group, a dimethylaminoethyl group, a methoxyethyl group, a cyclopropyl group, a cyclobutyl group, a cyclopentyl group, and a cyclohexyl group.

(D) Compounds of (A) or (B) or pharmaceutically-acceptable salts thereof, wherein $R^1$ and $R^2$ form, together with the nitrogen atom to which they bond, a morpholino group, a pyrrolidinyl group, a piperidinyl group, a piperazinyl group, a 3-fluoro-1-pyrrolidinyl group, a 3-hydroxy-1-pyrrolidinyl group, a 2-hydroxymethyl-1-pyrrolidinyl group, a 3,3-difluoro-1-pyrrolidinyl group, a 2-oxo-1-pyrrolidinyl group, a 3-oxo-1-pyrrolidinyl group, or a 4-methoxy-1-piperidinyl group.

(E) Compounds of (A) or (B) or pharmaceutically-acceptable salts thereof, wherein $R^{3a}$ and $R^{3b}$ are the same or different, and each represents a hydrogen atom, a methyl group or an ethyl group.

(F) Compounds of (A) or (B) or pharmaceutically-acceptable salts thereof, wherein $R^4$ is a hydrogen atom or a methyl group.

(G) Compounds of (A) or (B) or pharmaceutically-acceptable salts thereof, wherein $Y_1$ is —$CH_2$—, —O—$CH_2CH_2$— or —$OCH_2CH_2CH_2$—.

(H) Compounds of (A) or (B) or pharmaceutically-acceptable salts thereof, wherein $Ar_2$ is a group selected from a phenyl group, a 2-fluorophenyl group, a 3-fluorophenyl group, a 4-fluorophenyl group, a 4-chlorophenyl group, a 3,4-difluorophenyl group, a 2,4-difluorophenyl group, a 2-trifluoromethylphenyl group, a 3-trifluoromethylphenyl group, a 4-trifluoromethylphenyl group, a 4-methoxyphenyl group, a 4-methanesulfonylphenyl group, a 2-pyridinyl group, a 5-methyl-2-pyridinyl group, a 6-difluoromethyl-3-pyridinyl group, a 5-difluoromethyl-2-pyridinyl group, a 6-fluoro-3-pyridinyl group, a 5-fluoro-2-pyridinyl group, a 6-chloro-3-pyridinyl group, a 5-chloro-2-pyridinyl group, a 4-chloro-2-pyridinyl group, a 6-methoxy-3-pyridinyl group, a 6-methoxy-2-pyridinyl group, a 5-methoxy-2-pyridinyl group, a 6-difluoromethoxy-3-pyridinyl group, a 5-difluoromethoxy-2-pyridinyl group, a 5-trifluoromethyl-2-pyridinyl group, a 6-trifluoromethyl-3-pyridinyl group, a 4-methylsulfanyl-2-pyridinyl group, a 2-pyrimidinyl group, a pyrazinyl group and a 3-pyridazinyl group.

Preferred examples of the compounds of the invention are the following:

5-(Benzyloxy)-N-[4-(morpholinomethyl)phenyl]-1H-indole-2-carboxamide, 5-(Benzyloxy)-N-{4-[(diethylamino)methyl]phenyl}-1H-indole-2-carboxamide, 5-[(5-Chloro-2-pyridinyl)methoxy]-N-{4-[(diethylamino)methyl]phenyl}-1H-indole-2-carboxamide, 5-(Benzyloxy)-N-[3-methoxy-4-(morpholinomethyl)phenyl]-1H-indole-2-carboxamide, 5-(Benzyloxy)-N-{4-[(4-methoxypiperidino)methyl]phenyl}-1H-indole-2-carboxamide, 5-(Benzyloxy)-N-(4-{[isopropyl(methyl)amino]methyl}phenyl)-1H-indole-2-carboxamide, 5-(Benzyloxy)-N-[4-(piperidinomethyl)phenyl]-1H-indole-2-carboxamide, 5-(Benzyloxy)-N-[4-(1-pyrrolidinylmethyl)phenyl]-1H-indole-2-carboxamide, 5-(Benzyloxy)-N-(4-{[ethyl(2-methoxyethyl)amino]methyl}phenyl)-1H-indole-2-carboxamide, 5-(Benzyloxy)-N-(4-{[(2-methoxyethyl)(methyl)amino]methyl}phenyl)-1H-indole-2-carboxamide et al.

More preferred are the following:

5-(Benzyloxy)-N-{4-[(diethylamino)methyl]phenyl}-1H-indole-2-carboxamide, 5-(Benzyloxy)-N-[4-(1-pyrrolidinylmethyl)phenyl]-1H-indole-2-carboxamide, 5-(Benzyloxy)-N-[4-(morpholinomethyl)phenyl]-1H-indole-2-carboxamide, 5-[(5-chloro-2-pyridinyl)methoxy]-N-{4-[(diethylamino)methyl]phenyl}-1 H-indole-2-carboxamide, 5-(Benzyloxy)-N-(4-{[(2-methoxyethyl)(methyl)amino]methyl}phenyl)-1H-indole-2-carboxamide et al.

Methods for Producing Compounds of Formula [I]

The compounds of formula [I] can be produced, for example, according to the following Production Method 1 to Production Method 3, as suitably combined.

Production Method 1:

Reaction Formula 1:

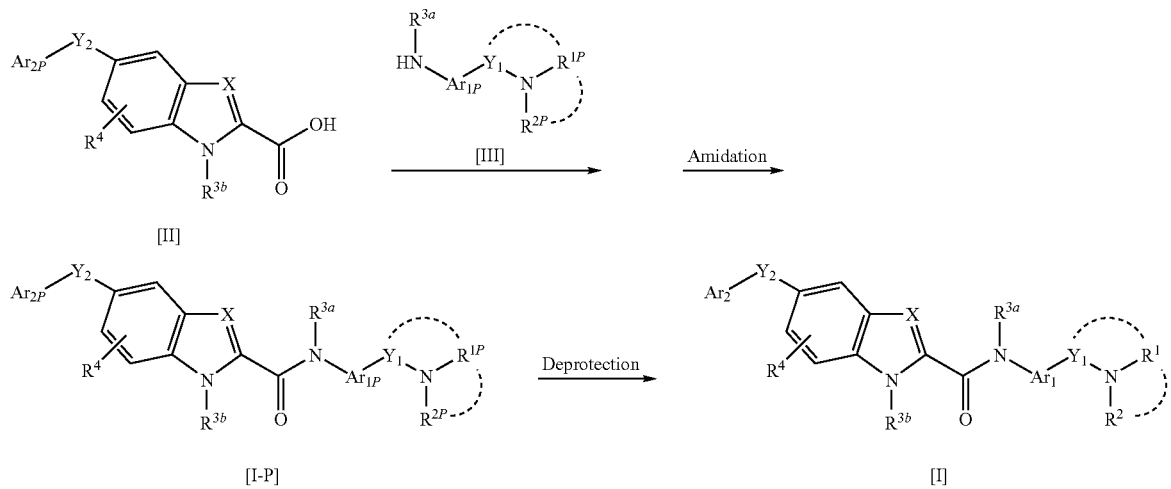

[wherein $R^{1P}$ represents $R^1$, or represents $R^1$ having a protective group; $R^{2P}$ represents $R^2$, or represents $R^2$ having a protective group; $Ar_{1P}$ represents $Ar_1$, or represents $Ar_1$ having a protective group; $Ar_{2P}$ represents $Ar_2$, or represents $Ar_2$ having a protective group; $R^{3a}$, $R^{3b}$, $R^4$, $Y_1$ and $Y_2$ have the same meanings as above.]

This method includes:

step 1-1: this is a step of amidating a compound of formula[II] with a compound of formula [III] in a solvent to give a compound of formula [I-P]; and step 1-2: this is a step of optionally removing the protective group, if any, from the product.

Step 1-1:

The amidation condensation may be attained according to any conventional known method used for peptide synthesis, for example, according to the method described in "Bases and Experiments of Peptide Synthesis" (by Nobuo Izumiya et al., Maruzen, 1983).

This reaction may be attained generally in an inert solvent, which includes, for example, halogenohydrocarbons such as methylene chloride, chloroform; ethers such as diethyl ether, tetrahydrofuran (hereafter abbreviated as "THF"), 1,4-dioxane (hereafter abbreviated as "dioxane"); acetonitrile, dimethylformamide (hereafter abbreviated as "DMF"), dimethylsulfoxide (hereafter abbreviated as "DMSO"), pyridine; or their mixed solvents.

The amidation is preferably attained in the presence of a condensing agent. The condensing agent includes, for example, N,N'-dicyclohexylcarbodiimide, 2-chloro-1,3-dimethyl-2-imidazolium chloride, N,N'-diisopropylcarbodiimide, 1-(3-dimethylaminopropyl)-3-ethylcarbodiimide, 1-(3-dimethylaminopropyl)-3-ethylcarbodiimide hydrochloride (hereafter abbreviated as "WSC·HCl"), benzotriazol-1-yloxy-tris-(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphorazide, 1,1'-carbonyldiimidazole, O-(7-azabenzotriazol-1-yl)-1,1,3,3-tetramethyluronium hexafluorophosphate (hereafter abbreviated as "HATU") et al.

The amount of the condensing agent to be used may be generally from one mol to an excessive molar amount per mol of the compound of formula [II], preferably from 1 mol to 1.5 mols.

The reaction temperature may be generally from $-50°$ C. to $100°$ C., preferably from $-20°$ C. to $50°$ C.

The reaction time may be generally from 30 minutes to 7 days, preferably from 1 hour to 24 hours.

In place of the carboxylic acid of formula [II], a reactive derivative of the carboxylic acid may be reacted with a compound of formula [III] to give a compound of formula [I].

The reactive derivative of the carboxylic acid of formula [II] includes, for example, halides, mixed acid anhydrides, active esters, active amides. These reactive derivatives may be readily prepared with reference to the above-mentioned "Bases and Experiments of Peptide Synthesis" (by Nobuo Izumiya et al., Maruzen, 1983).

Acid halides of the compound of formula [II] may be obtained by reacting the compound of formula [II] with a halogenating agent according to a conventional known method. The halogenating agent includes, for example, thionyl chloride, phosphorus trichloride, phosphorus pentachloride, phosphorus oxychloride, phosphorus tribromide, oxalyl chloride, phosgene et al.

Mixed acid anhydrides of the compound of formula [II] may be obtained according to a conventional known method, for example, by reacting the compound of formula [II] with an alkyl chlorocarbonate such as ethyl chlorocarbonate, isobutyl chlorocarbonate, or an aliphatic carboxylic acid chloride such as pivaloyl chloride, in the presence of an amine such as triethylamine.

Active esters of the compound of formula [II] may be obtained, for example, by reacting the compound of formula [II] with an N-hydroxy compound such as N-hydroxysuccinimide, N-hydroxyphthalimide, 1-hydroxybenzotriazole (hereafter abbreviated as "HOBt") or a phenolic compound such as 4-nitrophenol, 2,4-dinitrophenol, 2,4,5-trichlorophenol or pentachlorophenol, in the presence of a condensing agent such as N,N'-dicyclohexylcarbodiimide or 1-(3-dimethylaminopropyl)-3-ethylcarbodiimide et al according to a conventional known method.

Active amides of the compound of formula [II] may be obtained, for example, by reacting the compound of formula [II] with one equivalent of 1,1'-carbonyldiimidazole or 1,1'-carbonylbis(2-methylimidazole) et al according to a conventional known method.

The amount of the compound of formula [II] or its reactive derivative to be used may be generally from 0.5 mols to an excessive molar amount per mol of the compound of formula [III], preferably from 1 mol to 1.5 mols.

The amidation may go on in the absence of a base, but for smoothly promoting, the reaction is effected preferably in the presence of a base.

Especially in the reaction of using an acid halide or a mixed acid anhydride, for example, an organic base such as triethylamine, diisopropylethylamine, pyridine et al, or an inorganic base such as sodium hydroxide, potassium hydroxide, sodium carbonate, potassium carbonate, sodium hydrogencarbonate et al may be used.

The amount of the base to be used may be generally from 1 mol to an excessive molar amount per mol of the compound of formula [III], preferably from 1 mol to 4 mols; and when the base is a liquid, then the base may act also as a solvent.

In any reaction of using the above-mentioned reactive derivative, a basic catalyst such as dimethylaminopyridine may be used for promoting the reaction. The amount of the catalyst to be used may be from 0.1 mols to 5 mols per mol of the reactive derivative, preferably from 0.1 mols to 0.5 mols.

The reaction temperature when the reactive derivative is used may be generally from $-50°$ C. to $100°$ C., preferably from $-20°$ C. to $50°$ C.

The reaction time when the reactive derivative is used may be generally from 5 minutes to 7 days, preferably from 30 minutes to 24 hours.

Step 1-2:

When the compound of formula [I-P] has a protective group, then the protective group is removed to give a compound of formula [I].

The method of removing the protective group may vary, depending on the type of the protective group and on the stability of the compound of formula [I]. For example, according to the methods described in a reference [see Protective Groups in Organic Synthesis, by T. W. Greene, John Wiley & Sons (1981)) or according to methods similar thereto, the deprotection may be attained through solvolysis with an acid or a base of, for example, processing the protected compound with from 0.01 mols to a large excessive amount of an acid, preferably trifluoroacetic acid, formic acid or hydrochloric acid, or with from an equimolar amount to a large excessive amount of a base, preferably sodium hydroxide or potassium hydroxide; or through chemical reduction with a metal hydride complex or through catalytic reduction with a palladium-carbon catalyst or a Raney nickel catalyst.

The compound of formula [II] and the compound of formula [III] may be prepared according to the methods described in Examples.

Production Method 2:

Production method 2 is a method for producing a product where $Y_1$ and $R^1$ do not form a nitrogenous hetero ring. This method gives a compound of formula [1-2].

Reaction Formula 2:

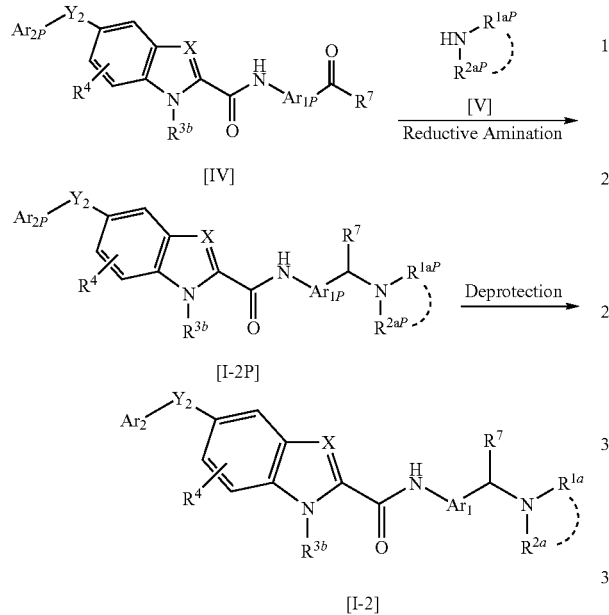

[wherein $R^{1a}$ and $R^{2a}$ are the same or different, and each represents a substituent selected from the following:
1) a $C_{1-6}$ alkyl group optionally substituted with $R^5$,
2) a $C_{3-8}$ cycloalkyl group optionally substituted with $R^6$, and
3) a 3- to 8-membered heterocycloalkyl group optionally substituted with $R^6$; or
$R^{1a}$ and $R^{2a}$ form, together with the nitrogen atom to which they bond, an aliphatic nitrogenous heterocyclic group optionally substituted with $R^6$;
$R^{1aP}$ represents $R^{1a}$, or represents $R^{1a}$ having a protective group; $R^{2aP}$ represents $R^{2a}$, or represents $R^{2a}$ having a protective group; $R^7$ represents a hydrogen atom or a $C_{1-6}$ alkyl group; $R^{3b}$, $R^4$, $Ar_1$, $Ar_{1P}$, $Ar_2$, $Ar_{2P}$, $Y_2$ and X have the same meanings as above.]

This method includes:

step 2-1: this is a step of reductive amination of a compound of formula [IV] with a compound of formula [V] in a solvent in the presence of sodium cyanotrihydroborate/zinc chloride to give a compound of formula [1-2P]; and step 2-2: this is a step of optionally removing the protective group, if any, from the compound of formula [1-2P].

In the step 2-1, the reductive amination may be attained according to a conventional known method (for example, as in J. Org. Chem., Vol. 50, 1927 (1985)). In the step 2-2, the deprotection may be the same as in the step 1-2.

The compound of formula [V] may be a commercially-available reagent, or may be prepared according to the methods described in Examples.

Production Method 3:

The production method 3 is for producing a compound of formula [IV].

Reaction Formula 3:

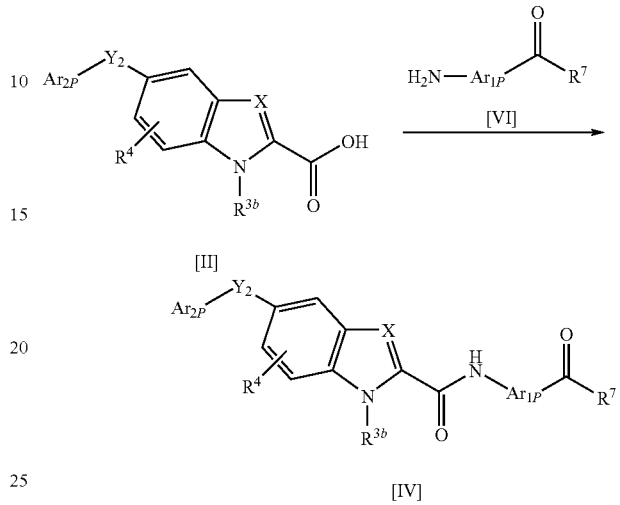

[wherein $R^{3b}$, $R^4$, $R^7$, X, $Y_2$, $Ar_{1P}$ and $Ar_{2P}$ have the same meanings as above.]

According to the method, a compound of formula [II] may be amidated with a compound of formula [IV] to give a compound of formula [IV]. The amidation may be the same as in the step 1-1. The compound of formula [VI] may be a commercially-available reagent.

In each reaction of the production method 1 to the production method 3, when the reactants have an amino group, a hydroxyl group, a carboxyl group, an oxo group, or a carbonyl group, which aren't participating in the reaction, then the amino group, the hydroxyl group, the carboxyl group, the oxo group and the carbonyl group may be suitably protected with a protective group for the amino group, a protective group for the hydroxyl group, a protective group for the carboxyl group, or a protective group for the oxo group or the carbonyl group, and the reaction of the production method 1 to the production method 3 is effected, and after the reaction, the protective group may be removed.

"Amino group-protective group" includes, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group. Especially preferred are an acetyl group, a pivaloyl group, a benzoyl group, an ethoxycarbonyl group, a tert-butoxycarbonyl group et al.

"Hydroxyl-protective group" includes, for example, a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group, a trimethylsilylethoxymethyl group; a tetrahydropyranyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group. Especially preferred are a methyl group, a methoxymethyl group, a tetrahydropyranyl group, a trityl group, a trimethylsilylethoxymethyl group, a tert-butyldimethylsilyl group, an acetyl group et al.

"Carboxyl-protective group" includes, for example, a lower alkyl group such as a methyl group, an ethyl group, a propyl group, an isopropyl group, a tert-butyl group; a lower haloalkyl group such as a 2,2,2-trichloroethyl group; a lower alkenyl group such as a 2-propenyl group; an aralkyl group such as a benzyl group, a p-methoxybenzyl group, a p-nitrobenzyl group, a benzhydryl group, a trityl group. Especially preferred are a methyl group, an ethyl group, a tert-butyl group, a 2-propenyl group, a benzyl group, a p-methoxybenzyl group, a benzhydryl group et al.

"Oxo or carbonyl-protective group" includes, for example, acetals and ketals such as ethylene ketal, trimethylene ketal, dimethyl ketal.

Removal of the protective group may vary depending on the type of the protective group and on the stability of the compound of formula [I]. For example, according to the methods described in a reference [see Protective Groups in Organic Synthesis, by T. W. Greene, John Wiley & Sons (1981)) or according to methods similar thereto, the deprotection may be attained through solvolysis with an acid or a base of, for example, processing the protected compound with from 0.01 mols to a large excessive amount of an acid, preferably trifluoroacetic acid, formic acid or hydrochloric acid, or with from an equimolar amount to a large excessive amount of a base, preferably sodium hydroxide or potassium hydroxide; or through chemical reduction with a metal hydride complex or through catalytic reduction with a palladium-carbon catalyst or a Raney nickel catalyst.

The compounds of formula (I) obtained in the manner as above may be readily isolated and purified in any conventional known separation method. The method includes, for example, solvent extraction, recrystallization, column chromatography, liquid chromatography or preparative thin-layer chromatography.

Depending on the type of the substituent therein, the compounds of formula [I] may be in any form of stereoisomers and tautomers such as optical isomers, diastereomers, geometrical isomers; and the compounds of the invention include all those stereoisomers and tautomers and their mixtures.

Pharmacological Test of Compounds of Formula [I]

The usefulness of the compounds of the invention as medicines is verified, for example, by the following pharmacological test example.

Pharmacological Test Example 1 (MCH Binding Inhibition Test)

A human MCH-1R encoding cDNA sequence [FEBS Letters, Vol. 398, 253 (1996); Biochimica et Biophisica Acta, Vol. 1401, 216 (1998)] was cloned to a plasmid vector pEF/mic/cyto (Invitrogen Corporation). The obtained expression vector was transfected to host cells CHO-K1 (American Type Culture Collection) using Lipofectamine Plus Reagent (Life Technology Inc.) to provide MCH-1R expression cells.

Membrane samples prepared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through a glass filter GF/C (Wattman Co.). After washing the glass filter with 50 mM Tris buffer (pH 7.4) comprising 10 mM magnesium chloride, 2 mM ethylenediamine tetraacetate and 0.04% Tween-20, the radioactive activity on the glass filter was measured. The non-specific binding was measured in the presence of 1 μM human MCH and 50% inhibition concentration ($IC_{50}$ value) of each test compound to the specific [$^{125}$I,]MCH binding was determined. The results are shown in Table 3.

TABLE 3

| Test Compound | $IC_{50}$ (nM) |
|---|---|
| Example 1-1 | 9.6 |
| Example 1-3 | 5.6 |
| Example 1-9 | 6.6 |
| Example 2-6 | 2.6 |
| Example 2-10 | 4.6 |

As in the above, it is understood that the compounds of the invention strongly inhibit the binding of MCH to MCH-1R, and therefore act as an MCH-1R antagonist.

Pharmaceutical Composition Comprising Compound of Formula [I]

The compound of the invention can be orally or parenterally administered, and can be formulated into preparations suitable to the administration thereof, which may be used as preventing or treating agents for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation; especially as preventing or treating agents for obesity.

In its clinical use, the compound of the invention may be formulated into various preparations along with a pharmaceutically-acceptable carrier added thereto in accordance with the administration route thereof, and the thus-formulated pharmaceutical composition may be administered. Various conventional additives known in the field of pharmaceutical preparations can be used as the carrier. For example, the carrier includes gelatin, lactose, white sugar, titanium oxide, starch, crystalline cellulose, hydroxypropylmethyl cellulose, carboxymethyl cellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid esters, polysorbate, sucrose fatty acid esters, polyoxyethylene, hardened castor oil, polyvinylpyrrolidone, magnesium stearate, light silicic anhydride, talc, vegetable oils, benzyl alcohol, gum arabic, propylene glycol, polyalkylene glycol, cyclodextrin and hydroxypropylcyclodextrin.

Preparations to be formed of a mixture of the carrier and the compound of the invention include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline water or glucose liquid, and a buffer or a preservative may be optionally added thereto.

The pharmaceutical compositions may contain the compound of the invention in an amount of from 1.0 to 100% by weight, preferably from 1.0 to 60% by weight of the composition, and may contain a pharmaceutically-acceptable carrier in an amount of from 0 to 99.0% by weight, preferably from 40 to 99.0% by weight. The compositions may further contain any other therapeutically-effective compound, for example, a remedial agent for diabetes, a remedial agent for hypertension, a remedial agent for arteriosclerosis, an anti-obesity agent.

In case where the compounds of the invention are used for prevention, treatment or remedy of the above-mentioned diseases or disorders, then the dose and the dosing frequency may be varied, depending on the sex, the age, the body weight and the disease condition of the patient and on the type and the range of the intended remedial effect. In general, the dose may be from 0.001 to 50 mg/kg of body weight/day, and it may be administered at a time or in a few times. The dose is preferably from about 0.01 to about 25 mg/kg/day, more preferably from about 0.05 to about 10 mg/kg/day.

Combination Therapy

The compounds of the invention can be used in combination with drugs effective for hypertension, obesity-associated hypertension, hypertension-associated diseases, hypertrophy, left ventricular hypertrophy, metabolic disorders, obesity, obesity-associated diseases and the like (hereafter referred to as "co-drugs"). Such drugs can be administered simultaneously, separately or in succession, for prevention or treatment of the above-mentioned diseases. When a compound of the invention is used simultaneously with one, two or more of co-drugs, they may be formulated into a medical preparation suited for single administration form. Whereas, in combination therapy, a composition containing the compound of the invention and co-drug(s) may be administered to the object of medication in different packages, either simultaneously, separately or successively. They may be administered at time interval(s).

The dose of the co-drug may be determined in accordance with the clinically adopted dose thereof, which can be suitably selected according to the individual object of medication, the administration route, the specific disease, the combination of drugs, and the like. The form of the co-drug for administration is not specifically defined, and it may be combined with the compound of the invention when they are administered. The administration mode includes, for example, the following: (1) A compound of the invention is combined with a co-drug to give a single preparation for single administration; (2) a compound of the invention and a co-drug are separately formulated into different two preparations, and the two preparations are simultaneously administered in one administration route; (3) a compound of the invention and a co-drug are separately formulated into different two preparations, and they are administered at different times in one and the same administration route; (4) a compound of the invention and a co-drug are separately formulated into different two preparations, and they are administered at the same time in two different administration routes; (5) a compound of the invention and a co-drug are separately formulated into different two preparations, and they are administered at different times in different administration routes (for example, a compound of the invention and a co-drug are administered in that order, or in an order contrary to this). The blend ratio of the compound of the invention and the co-drug may be suitably determined depending on the administration object, the administration route, and the disease for the administration.

The co-drugs usable in the invention include, for example, "drugs for diabetes", "drugs for hyperlipidemia", "drugs for hypertension", "anti-obesity drugs". Two or more such co-drugs may be combined in an adequate ratio and used.

"Drugs for diabetes" include, for example, 1) PPAR-γ agonists such as glitazones (e.g., ciglitazone, darglitazone, englitazone, isaglitazone, MCC-555), pioglitazone, rosiglitazone, troglitazone, BRL49653, CLX-0921, 5-BTZD, GW-0207, LG-100641, LY-300512; 2) biguanides such as metformin, buformin, phenformin; 3) protein tyrosine phosphatase 1B inhibitors; 4) sulfonylureas such as acetohexamide, chloropropamide, diabinese, glibenclamide, glipizide, glyburide, glimepiride, glicilazide, glipentide, gliquidone, glisolamide, trazamide, tolubutamide; 5) meglitinides such as repaglinide, nateglinide; 6) α-glucoside hydrolase inhibitors such as acarbose, adiposine, camiglibose, emiglitate, miglitol, voglibose, pradimicin-Q, salbostatin, CKD-711, MDL-25, 673, MDL-73, 945, MOR14; 7) α-amylase inhibitors such as tendamistat, trestatin, A13688; 8) insulin secretion promoters such as linogliride, A-4166; 9) fatty acid oxidation inhibitors such as clomoxir, etomoxir; 10) A2 antagonists such as midaglizole, isaglidole, deriglidole, idazoxan, earoxan, fluparoxan; 11) insulin or insulin mimetics such as biota, LP-100, novalapid, insulin determir, insulin lispro, insulin glargine, insulin zinc, Lys-Pro-insulin, GLP-1 (73-7), GLP1 amide (7-36); 12) non-thiazolidinediones such as JT-501, farglitazar; 13) PPARα/γ dual-agonists such as MK-0767, CLX-0940, GW-1536, GW-1929, GW-2433, KRP-297, L-796449, LR-90 and SB219994.

"Drugs for hyperlipidemia" include, for example, 1) bile acid absorption promoters such as cholesterylamine, colesevelem, colestipol, crosslinked dextran dialkylaminoalkyl derivatives, Colestid™, LoCholest™, Questran™; 2) HMG-CoA reductase inhibitors such as atorvastatin, itavastatin, fluvastatin, lovastatin, pravastatin, rivastatin, rosuvastatin, simvastatin, ZD-4522; 3) HMG-CoA synthase inhibitors; 4) cholesterol absorption inhibitors such as snatol ester, β-sitosterol, sterol glucoside, ezetimibe; 5) acyl-coenzyme A cholesterol acyl transferase inhibitors such as avasimibe, eflucimibe, KY-505, SMP-709; 6) CETP inhibitors such as JTT705, torcetrapib, CP532632, BAY-63-2149, SC-591, SC-795; 7) squalane synthesis inhibitors; 8) antioxidants such as probucol; 9) PPAR-α agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid™, Lopid™, Tricor™); 10) FXR receptor antagonists such as GW-4064, SR-103912; 11) LXR receptor agonists such as GW3965, T9013137, XTCO-179628; 12) lipoprotein synthesis inhibitors such as niacin; 13) renin-angiotensin system inhibitors; 14) microsome-triglyceride transport inhibitors; 15) bile acid resorption inhibitors such as BARA1453, SC435, PHA384640, S-435, AZD7706; 16) PPAR-δ agonists such as GW501516, GW590735; 17) triglyceride synthesis inhibitors; 18) MTTP inhibitors such as LAB687, CP346086; 19) low-density lipoprotein receptor inducers; 20) squalane epoxidase inhibitors; 21) platelet agglutination inhibitors; 22) 5-lipoxygenase activated protein inhibitors such as MK-591.

"Drugs for hypertension" include, for example, 1) thiazide diuretics such as chlorothialidon, chlorothiazide, dichlorofenamide, hydrofluorothiazide, indapamide, hydrochlorothiazide; loop diuretics such as bumetanide, ethacrynic acid, flosemide, tolusemide; sodium diuretics such as amyloride, triamuteren; aldosterone antagonist diuretics such as spironolactone, epilenone; 2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tartatolol, tilisolol, timolol; 3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil; 4) angiotensin converting enzyme inhibitors such as benazepril, captopril, cilazapril, delapril, enalapril, fosinopril, imidapril, rosinopril, moexipril, quinapril, quinaprilat, ramipril, perindopril, perindoropril, quanipril, spirapril, tenocapril, transolapril, zofenopril; 5) neutral endopeptidase inhibitors such as omapatrilat, cadoxatril, ecadotril, fosidotril, sampatrilat, AVE7688, ER4030; 6) endothelin antagonists such as tezosentan, A308165, YM62899; 7) vasodilators such as hydraladine, clonidine, minoxidil, nicotinyl alcohol; 8) angiotensin II antagonists such as candesartan, eporsartan, iribesartan, losartan, pratosartan, tasosartan, telmisartan, balsartan, EXP-3137, F16828K, RNH6270; 9) α/β adrenalin blockers such as nipradilol, arotinolol, amoslalol; 10) α1 blockers such as terazosin, urapidil, prazosin, bunazosin, trimazosin, doxazosin, naphthopidil, indolamin, WHIP164, XEN010; 11) α2 agonists such as lofexidine, tiamenidine, moxonidine, rilmenidine, guanobenz; and 12) aldosterone inhibitors.

"Anti-obesity drugs" include, for example, 1) 5HT (serotonin) transporter inhibitors such as paroxetine, fluoxetine, fenfluramine, fluvoxamine, sertraline, imiplamin; 2) norepinephrine transporter inhibitors such as GW320659, desipramine, talsupramine, nomifensin; 3) cannabinoid-1 receptor 1 (CB-1) antagonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, EP-658546; 4) glerin antagonists such as compounds disclosed in WO01/87355, WO02/08250; 5) histamine(H3) antagonists/inverse-agonists such as thioperamide, 3-(1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Pharmazie, 56: 927-32 (2001)), benzophenone derivatives (Sasse, A. et al., Arch. Pharm. (Weinheim) 334: 45-52 (2001)), substituted N-phenylcarbamates (Reidemeister, S. et al., Pharmazie, 55: 83-6 (2000)), proxyfen derivatives (Sasse, A. et al., J. Med. Chem., 43: 3335-43 (2000)); 6) MCH-1R antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, JP-A 2001-226269; 7) MCH-2R agonists/antagonists; 8) NPY1 antagonists such as isopropyl 3-chloro-5-(1-(6-[2-(5-ethyl-4-methyl-thiazol-2-yl)-ethyl]-4-morpholinyl-4-yl-piperidin-2-ylamino)-ethyl)phenyl] carbamate, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173, WO01/89528; 9) NPY5 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298, 6,337,332, 6,329,395, 340,683, 6,326,375, 6,329,395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., J. Med. Chem., 43:4288-4312(2000);10) reptins such as human recombinant reptin (PEG-OB, Hoffman La Roche), recombinant methionylreptin (Amgen); 11) reptin derivatives such as compounds disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519, WO96/23520; 12) opioid antagonists such as narmefen (Revex™), 3-methoxynartorexon, naloxon, nartolexon, compounds disclosed in WO00/21509; 13) aurexin antagonists such as SB-334867A, and other compounds disclosed in WO01/96302, WO01/68609, WO02/51232, WO02/51838, WO03/023561; 14) bonbesin receptor subtype-3 agonists; 15) cholecystokinin A (CCK-A) agonists such as AR-R15849, GI-181771, JMV-180, A-71378, A-71623, SR-146131, and other compounds disclosed in U.S. Pat. No. 5,739,106; 16) CNTF (ciliary neurotrophic factors) such as GI-181771 (Glaxo-Smith Kline), SR146131 (Sanofi Synthelabo), butabindide, PD170,292, PD 149164 (Pfizer); 17) CNTF derivatives such as axokine (Regeneron), and other compounds disclosed in WO94/09134, WO98/22128, WO99/43813; 18) growth hormone secretion receptor agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888; 19) serotonin receptor-2C agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457; 20) melanocortin-3 receptor agonists; 21) melanocortin-4 receptor agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847; 22) monoamine resorption inhibitors such as sibutramine (Meridia™/Recuctil™) and its salts, and other derivatives disclosed in U.S. Pat. Nos. 4,746,680, 4,806,570, 5,436,272, US Patent Application No. 2002/0006964, WO01/27068, WO01/62341; 23) serotonin re-uptake inhibitors such as dexfenfluramine, fluoxetine, and other compounds disclosed in U.S. Pat. No. 6,365,633, WO01/27060, WO01/162341; 24) glucagon-like peptide-1 agonists; 25) topiramate (Topimax™); 26) phytopharm compound 57 (e.g., CP644,673); 27) acetyl CoA carboxylase-2 (ACC2) inhibitors; 28) β-adrenalin receptor-3 agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. Nos. 5,705,515, 5,451,677, WO01/74782, WO02/32898; 29) diacylglycerol acyltransferase-1 inhibitors; 30) diacylglycerol acyltransferase-2 inhibitors, 31) fatty acid synthesis inhibitors such as carulenin, C75; 32) phosphodiesterase inhibitors such as theophylline, pentoxifylline zaprinast, sildenafil, amrinone, milrinone, cilostamide, rolipram, cilomilast; 32) thyroid hormone-β agonists such as KB-2611 (KaroBio BMS), and other compounds disclosed in WO02/15845, JP-A 2000-256190; 33) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TT-NPB), retinoic acid, and other compounds disclosed in WO99/00123; 34) acylestrogens such as oleoylestrone, and other compounds disclosed in del Mar-Grasa, M. et al., Obesity Research, 9:202-9 (2001); 35) glucocorticoid antagonists; 36) 11-β-hydroxysteroid dehydrogenase-1 inhibitors such as BVT3498, BVT2733, and other compounds disclosed in WO01/90091, WO01/90090, WO01/90092; 37) stearoyl-CoA desaturase-1 inhibitors; 38) dipeptidyl peptidase-IV inhibitors such as isoleucine thiazolidine, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002593, WO03/000180, WO03/000181; 39) lipase inhibitors such as tetrahydroliptatin (Orlistat/Xenical™), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. Nos. 4,598,089, 4,452,813, 5,512,565, 5,391,571, 5,602,151, 4,405,644, 4,189,438, 4,242,453; 39) fatty acid transporter inhibitors; 40) dicarboxylate transporter inhibitors; 41) glucose transporter inhibitors; 42) phosphate transporter inhibitors.

Those combination drugs are obtained by concurrent use of a compound of the invention with one, two or more of the above co-drugs. Furthermore, the combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and anti-obesity agent are useful for prevention, treatment or therapy of metabolic disorders with synergistic effect, when diabetes-treating agent(s) and/or hyperlipidemia-treating agent(s) are added thereto.

BEST MODE FOR CARRYING OUT THE INVENTION

The invention is described in detail with reference to the following Examples, to which, however, the invention should not be limited. Unless otherwise specifically indicated, the reagents used in the Examples are commercial products. In H-NMR, tetramethylsilane was used as the standard substance.

REFERENCE EXAMPLE 1-1

Production of 5-(benzyloxy)-1-methyl-1H-indole-2-carboxylic acid (1) At 0° C., sodium hydride (449 mg) was added to a DMF solution (10 mL) of 5-benzyloxyindole-2-carboxylic acid (1.0 g), and stirred for 10 minutes, and then methyl iodide (980 μL) was added thereto and stirred overnight at room temperature. Water was added to the reaction liquid, extracted with diethyl ether, and the organic layer was washed with water and saturated saline water in that order, then dried with anhydrous sodium sulfate. The organic layer was concentrated under reduced pressure, and the resulting crystal was washed with hexane to obtain methyl 5-(benzyloxy)-1-methyl-1H-indole-2-carboxylate (792 mg) as a yellow solid.

ESI-MS Found: m/z 296[M+H]$^+$.

(2) At 0° C., aqueous 1 N sodium hydroxide solution (3.0 mL) was added to a methanol solution (20 mL) of the obtained compound (600 mg), and stirred at room temperature for 2 hours. Further, aqueous 4 N sodium hydroxide solution (760 μL) was added to the reaction liquid, and stirred for 3 days at room temperature. The reaction liquid was concentrated under reduced pressure, water was added to the residue and extracted with diethyl ether. The aqueous layer was made acidic with aqueous 10% phosphoric acid added thereto, and then extracted with chloroform. The organic layer was washed with saturated saline water, and then dried with anhydrous sodium sulfate. The organic layer was concentrated under reduced pressure, and the resulting crystal was washed with hexane to obtain the entitled compound (221 mg) as a white solid.

ESI-MS Found: m/z 282[M+H]$^+$, 280[M−H]$^−$.

REFERENCE EXAMPLE 1-2

Production of 5-(2-pyridinylmethoxy)-1H-indole-2-carboxylic acid (1) A 4 N hydrogen chloride-methanol solution (80 mL) of 5-hydroxyindole-2-carboxylic acid (3.0 g) was heated overnight under reflux. The solvent was evaporated off from the reaction liquid under reduced pressure, aqueous saturated sodium hydrogencarbonate solution was added to the resulting residue, and extracted with ethyl acetate. The organic layer was dried with anhydrous magnesium sulfate, and the solvent was evaporated off under reduced pressure. The resulting residue was purified through silica gel column chromatography (hexane/ethyl acetate=4/1 to 3/2) to obtain methyl 5-hydroxy-1H-indole-2-carboxylate (2.3 g) as a pale brown solid.

ESI-MS Found: m/z 192[M+H]$^+$.

(2) 2-Chloromethylpyridine hydrochloride (515 mg) and potassium carbonate (1.3 g) were added to a DMF solution (30 mL) of the obtained compound (600 mg), and stirred overnight at room temperature. Water was added to the reaction liquid, and extracted with ethyl acetate. The organic layer was dried with anhydrous magnesium sulfate, and the solvent was evaporated off under reduced pressure. The resulting residue was purified through silica gel column chromatography (hexane/ethyl acetate=4/1) to obtain methyl 5-(2-pyridinylmethoxy)-1H-indole-2-carboxylate (160 mg) as a white solid.

ESI-MS Found: m/z 283[M+H]$^+$.

(3) Aqueous 5 N sodium hydroxide solution (1.6 mL) was added to a mixed solution of the compound (220 mg) obtained in the above, in methanol (1.0 mL) and THF (1.5 mL), and stirred overnight at room temperature. 5 N hydrochloric acid (1.8 mL) was added to the reaction liquid, and stirred at room temperature for 5 minutes. The organic solvent was evaporated off under reduced pressure from the reaction liquid, and the resulting residue was taken out through filtration and dried under reduced pressure to obtain the entitled compound (200 mg) as a pale yellow solid.

ESI-MS Found: m/z 269[M+H]$^+$.

REFERENCE EXAMPLE 1-3

Production of 5-[(6-chloro-3-pyridinyl)methoxy]-1H-indole-2-carboxylic acid

The entitled compound was obtained as a pale yellow solid in the same manner as in Reference Example 1-2-(2) and (3) but using 2-chloro-5-chloromethylpyridine and the compound obtained in Reference Example 1-2-(1).

ESI-MS Found: m/z 303[M+H]$^+$.

REFERENCE EXAMPLE 1-4

Production of 5-[(5-chloro-2-pyridinyl)methoxyl]-1H-indole-2-carboxylic acid

The entitled compound was obtained as a pale yellow solid in the same manner as in Reference Example 1-2-(2) and (3) but using 2-chloromethyl-5-chloropyridine and the compound obtained in Reference Example 1-2-(1).

ESI-MS Found: m/z 303[M+H]$^+$.

REFERENCE EXAMPLE 1-5

Production of 5-{[5-(trifluoromethyl)-2-pyridinyl]methoxy]-1H-indole-2-carboxylic acid The entitled compound was obtained as a white solid in the same manner as in Reference Example 1-2-(2) and (3) but using 2-chloromethyl-5-trifluoromethylpyridine and the compound obtained in Reference Example 1-2-(1).

ESI-MS Found: m/z 337[M+H]$^+$.

REFERENCE EXAMPLE 1-6

Production of 5-(benzyloxy)-1H-benzimidazole-2-carboxylic acid (1) At 0° C., diethyl azodicarboxylate (3.4 mL) was added to a THF solution (13 mL) of 4-amino-3-nitrophenol (1.0 g), benzyl alcohol (1.0 g) and triphenyl phosphine (1.9 g), and stirred at room temperature for 5 hours. The reaction liquid was diluted with ethyl acetate, and the organic layer was washed with aqueous 1 N sodium hydroxide solution, aqueous saturated sodium hydrogencarbonate solution and saturated saline water in that order. The organic layer was dried with anhydrous sodium sulfate, and then concentrated under reduced pressure. The resulting residue was purified through silica gel column chromatography (hexane/ethyl acetate=2/8 to 3/7) to obtain 4-(benzyloxy)-2-nitroaniline (1.2 g) as a red solid.

ESI-MS Found: m/z 245[M+H]$^+$.

(2) Powdery iron (1.4 g) and ammonium chloride (1.3 g) were added to a mixed solution of the obtained compound (6.0 mL), tetrahydrofuran (12 mL) and water (6.0 mL), and stirred at 80° C. for 3 hours. The reaction liquid was diluted with ethyl acetate, then filtered through Celite, and the filtrate was washed with aqueous saturated sodium hydrogencarbonate solution and saturated saline water. The organic layer was dried with anhydrous magnesium sulfate, and then concentrated under reduced pressure. The resulting residue was purified through silica gel column chromatography (ethyl acetate) to obtain 4-(benzyloxy)-1,2-benzenediamine (1.0 g) as a black solid.

ESI-MS Found: m/z 215[M+H]$^+$.

(3) WSC·HCl (559 mg) was added to a pyridine solution (13 mL) of the obtained compound (521 mg) and glycolic acid (189 mg), and stirred at room temperature for 4 hours. The reaction liquid was diluted with water, and then extracted with ethyl acetate. The organic layer was washed with aqueous saturated sodium hydrogencarbonate solution and saturated saline water, then dried with anhydrous magnesium sulfate. The organic layer was concentrated under reduced pressure to obtain a residue (559 mg) as a brown solid.

ESI-MS Found: m/z 273[M+H]$^+$.

At room temperature, potassium tert-butoxide (763 mg) was added to an isopropyl alcohol solution (20 mL) of the residue (559 mg), stirred at 60° C. for 1.5 hours, and then overnight at 80° C. Next, at 0° C., 0.7 N hydrochloric acid (23 mL) was added to the reaction liquid, and stirred for 1 hour, and a hardly-soluble compound was filtered away. The filtrate was extracted with ethyl acetate, and the organic layer was washed with aqueous saturated sodium hydrogencarbonate solution and saturated saline water. The organic layer was dried with anhydrous magnesium sulfate, and then concentrated under reduced pressure. The residue was purified through reversed-phase preparative column chromatography, then diluted with chloroform, and the organic layer was washed with aqueous saturated sodium hydrogencarbonate solution and saturated saline water. The organic layer was dried with anhydrous magnesium sulfate, then concentrated under reduced pressure to obtain [5-(benzyloxy)-1H-benzimidazol-2-yl]methanol (158 mg) as an yellow solid.

ESI-MS Found: m/z 255[M+H]$^+$.

(4) At 120° C., potassium permanganate (147 mg) was added to an aqueous solution (3.0 mL) of the compound (158 mg) obtained in (3) and sodium carbonate (16 mg), and stirred for 1 hour. After cooled, this was filtered through Celite, and 0.5 N hydrochloric acid was added to the filtrate. The resulting crystal was taken out through filtration, and washed with water to obtain the entitled compound (56 mg) as a brown solid.

ESI-MS Found: m/z 269[M+H]$^+$.

REFERENCE EXAMPLE 2-1

Production of N-(4-aminobenzyl)-N,N-diethylamine dihydrochloride (1) P-nitrobenzyl bromide (5.0 g) was added to a methanol solution (50 mL) of diethylamine (16.9 g), and stirred at room temperature for 3 hours. Methanol was evaporated off from the reaction liquid under reduced pressure, and water was added to the resulting residue, and extracted with ethyl acetate. The organic layer was extracted with 1 N hydrochloric acid, and the aqueous layer was neutralized with aqueous ammonium solution. The aqueous layer was extracted with ethyl acetate, and the organic layer was dried with anhydrous magnesium sulfate, and then the solvent was evaporated off under reduced pressure to obtain N,N-diethyl-N-(4-nitrobenzyl)amine (4.8 g) as an orange oily substance.

ESI-MS Found: m/z 209[M+H]$^+$.

(2) Raney nickel (50% slurry/water, 2.0 g) was added to an ethanol solution (100 mL) of the obtained compound (5.4 g), and in a hydrogen atmosphere (about 101.3 KPa), this was stirred at room temperature for 1 hour. The reaction liquid was filtered through Celite, and the solvent was evaporated off from the filtrate under reduced pressure. Then, 5 N hydrochloric acid was added to it, and vigorously stirred at room temperature. Water was evaporated off under reduced pressure from the reaction liquid, and the residue was dried under reduced pressure to obtain the entitled compound (5.0 g) as a light brown solid.

ESI-MS Found: m/z 179[M+H]$^+$.

REFERENCE EXAMPLE 2-2

Production of 4-(morpholinomethyl)aniline dihydrochloride

The entitled compound was obtained as a light brown solid in the same manner as in Reference Example 2-1-(1) and (2) but using morpholine.

ESI-MS Found: m/z 193[M+H]$^+$.

REFERENCE EXAMPLE 2-3

Production of 3-methoxy-4-(morpholinomethyl)aniline (1) Thionyl chloride (11.1 mL) was added to a dichloromethane solution (20 mL) of 2-methoxy-4-nitrobenzoic acid (500 mg) and heated under reflux for 2 hours. The solvent was evaporated off under reduced pressure from the reaction liquid, and chloroform (5 mL) was added to the residue. The chloroform solution was dropwise added to a THF solution (10 mL) of morpholine (2.2 g), and after the addition, this was stirred overnight at room temperature. The solvent was evaporated off under reduced pressure from the reaction liquid, and water was added to the resulting residue, and extracted with ethyl acetate. The organic layer was dried with anhydrous magnesium sulfate, and the solvent was evaporated off under reduced pressure. The resulting residue was purified through silica gel column chromatography (hexane/ethyl acetate=3/2) to obtain (2-methoxy-nitrophenyl)(morpholino)methanone (280 mg) as a white solid.

ESI-MS Found: m/z 267[M+H]$^+$.

(2) A THF solution (2.6 mL) of 2 M borane-methyl sulfide complex was added to a THF solution (5.0 mL) of the obtained compound (280 mg), and heated overnight under reflux. The solvent was evaporated off under reduced pressure from reaction liquid, and methanol (10 mL) was added to the resulting residue, and heated under reflux for 8 hours. The solvent was evaporated off under reduced pressure from the reaction liquid, and the resulting residue was purified through silica gel column chromatography (hexane/ethyl acetate=3/2) to obtain 4-(2-methoxy-4-nitrobenzyl)morpholine (230 mg) as an yellow oily substance.

ESI-MS Found: m/z 253[M+H]$^+$.

(3) Raney nickel (50% slurry/water, 200 mg) was added to an ethanol solution (5.0 mL) of the above compound (110 mg), and in a hydrogen atmosphere (about 101.3 KPa), this was stirred at room temperature for 1 hour. The reaction liquid was filtered through Celite, and the solvent was evaporated off from the filtrate under reduced pressure to obtain the entitled compound (90 mg) as an yellow oily substance.

ESI-MS Found: m/z 223[M+H]$^+$.

REFERENCE EXAMPLE 2-4

Production of 4-[2-(dimethylamino)ethyl]aniline (1) Aqueous 4 N sodium hydroxide solution (11 mL) and di-tert-butyl dicarbonate (6.5 g) were added to a DMF solution (20 mL) of 4-aminophenylacetic acid (3.0 g), and stirred at room temperature for 1.5 hours. Further, tert-butyl dicarbonate (13.0 g) was added to it, and stirred at room temperature for 1 hour. Water and aqueous 4 N sodium hydroxide solution were added to the reaction liquid, and extracted with diethyl ether. Then, the aqueous layer was made acidic with aqueous 10% phosphoric acid solution added thereto, and thereafter extracted with diethyl ether. The diethyl ether layers were combined, washed with water and saturated saline water, and then dried with anhydrous sodium sulfate. The organic layer was concentrated under reduced pressure to obtain 2-{4-[(tert-butoxycarbonyl)amino]phenyl}acetic acid (4.3 g) as a white solid.

ESI-MS Found: m/z 252[M+H]$^+$, 250[M−H]$^-$.

(2) Diethylamine (690 μL), HOBT hydrate (1.4 g), WSC·HCl (1.7 g) and triethylamine (2.5 mL) were added to a DMF solution (28 mL) of the above compound (1.5 g), and stirred overnight at room temperature. Water was added to the reaction liquid, and extracted with ethyl acetate. The organic layer was washed with water and saturated saline water, and then dried with anhydrous sodium sulfate. The organic layer was concentrated under reduced pressure, and the residue was purified through silica gel column chromatography (hexane/ethyl acetate=6/4 to 3/7) to obtain tert-butyl N-{4-[2-(dimethylamino)-2-oxoethyl]phenyl}carbamate (1.0 g) as a white solid.

ESI-MS Found: m/z 307[M+H]$^+$.

(3) Trifluoroacetic acid (4.0 mL) was added to the obtained compound (250 mg), and stirred at room temperature for 30 minutes. Trifluoroacetic acid was evaporated off from the reaction liquid under reduced pressure, and aqueous 4 N sodium hydroxide solution was added to the resulting residue at 0° C., and extracted with chloroform. The organic layer was washed with saturated saline water, and dried with anhydrous sodium sulfate. The organic layer was concentrated under reduced pressure, and the residue was dissolved in THF (5.0 mL), and at 0° C., lithiumaluminium hydride (93 mg) was added thereto. The reaction liquid was stirred at 70° C. for 30 minutes, and then sodium sulfate 10-hydrate was added thereto to stop the reaction. The reaction liquid was dried with anhydrous sodium sulfate added thereto, and then filtered through Celite. The filtrate was concentrated under reduced pressure to obtain a residue containing the entitled compound (122 mg). Not purified, the residue was used in Example 1-4.

ESI-MS Found: m/z 193[M+H]$^+$.

REFERENCE EXAMPLE 2-5

Production of 4-[(diethylamino)methyl]-N-methylaniline (1) At 0° C., ethyl chloroformate (455 μL) was added to a chloroform solution (13 mL) of N-(4-aminobenzyl)-N,N-diethylamine dihydrochloride (1.0 g) obtained in Reference Example 2-1-(2) and triethylamine (2.2 mL), and stirred at 0° C. for 1.5 hours and then at room temperature for 2 hours. Aqueous sodium hydrogencarbonate solution was added to the reaction liquid to stop the reaction, and this was extracted with chloroform. The organic layer was washed with water and saturated saline water, and then dried with anhydrous sodium sulfate. The organic layer was concentrated under reduced pressure, and the residue was purified through silica gel column chromatography (chloroform/methanol=9/1) to obtain ethyl N-{4-[(diethylamino)methyl]phenyl}carbamate (530 mg) as an orange oily substance.

ESI-MS Found: m/z 251[M+H]$^+$.

(2) At 0° C., lithiumaluminium hydride (91 mg) was added to a THF solution (4.0 mL) of the obtained compound (300 mg), and stirred at room temperature for 1 hour and then at 60° C. for 1 hours. Sodium sulfate 10 hydrate was added to the reaction liquid at 0° C. to stop the reaction, and then this was dried with anhydrous sodium sulfate. The reaction mixture was filtered through Celite, and the filtrate was concentrated under reduced pressure to obtain a residue containing the entitled compound (210 mg). Not purified, the residue was used in Example 1-5.

ESI-MS Found: m/z 193[M+H]$^+$.

REFERENCE EXAMPLE 2-6

Production of N-(5-amino-2-pyridinyl)-N-[2-(dimethylamino)ethyl]-N-methylamine (1) Potassium carbonate (2.0 g) and N,N,N'-trimethylethylenediamine (1.1 g) were added to a DMF solution (20 mL) of 2-bromo-5-nitropyridine (2.0 g), and stirred at 80° C. for 2 hours. The solvent was evaporated off under reduced pressure from the reaction liquid, and the resulting residue was purified through silica gel column chromatography (chloroform/methanol=500/5 to 500/10) to obtain N-[2-(dimethylamino)ethyl]-N-methyl-N-(5-nitro-2-pyridinyl)amine (1.35 g) as an yellow oily substance.

ESI-MS Found: m/z 225[M+H]$^+$.

(2) 10% Pd/C was added to a methanol solution (5.0 mL) of the obtained compound (200 mg), and in a hydrogen atmosphere (about 101.3 KPa), this was stirred at room temperature for 1 hour. The reaction liquid was filtered through Celite, and the filtrate was concentrated under reduced pressure to obtain the entitled compound (150 mg) as a yellow oily substance.

ESI-MS Found: m/z 195[M+H]$^+$.

REFERENCE EXAMPLE 2-7

Production of N-(5-amino-2-pyridinyl)-N-isopropyl-N-methylamine

The entitled compound was obtained as a yellow oily substance in the same manner as in Reference Example 2-6-(1) and (2) but using N-isopropyl-N-methylamine.

ESI-MS Found: m/z 195[M+H]$^+$.

EXAMPLE 1-1

Production of 5-(benzyloxy)-N-[4-(morpholinomethyl)phenyl]-1H-indole-2-carboxamide hydrochloride Diisopropylethylamine (275 μL) was added to a DMF solution (800 μL) of 5-hydroxyindole-2-carboxylic acid (211 mg), the compound (167 mg) obtained in Reference Example 2-2, and HATU (304 mg), and stirred at room temperature for 3 days. The reaction liquid was diluted with chloroform, and the organic layer was washed with aqueous 1 N sodium hydroxide solution. The organic layer was concentrated under reduced pressure, and the residue was purified through reversed-phase preparative column chromatography. The organic layer was diluted with chloroform, then washed with aqueous saturated sodium hydrogencarbonate solution, aqueous 1 N sodium hydroxide solution and saturated saline water. The organic layer was dried with anhydrous magnesium sulfate, and then concentrated under reduced pressure to obtain a free form of the entitled compound (306 mg) as a white solid.

4 N hydrogen chloride-ethyl acetate solution (800 μL) was added to an ethyl acetate solution (100 mL) of the free form of the entitled compound (306 mg), and stirred at room temperature for 20 minutes. The resulting precipitate was taken out through filtration and washed to obtain the entitled compound (307 mg) as a colorless solid.

$^1$H-NMR (400 MHz, CD$_3$OD, δ ppm): 3.15-3.42 (4H, m), 3.63-4.15 (4H, m), 4.31 (2H, s), 5.09 (2H, s), 7.00 (1H, dd, J=8.8, 2.2 Hz), 7.17 (1H, d, J=2.2 Hz), 7.22 (1H, s), 7.26-7.31 (1H, m), 7.33-7.38 (3H, m), 7.46-7.43 (2H, m), 7.49 (2H, d, J=8.8 Hz), 7.87 (2H, d, J=8.8 Hz).

ESI-MS Found: m/z 442[M+H]$^+$.

EXAMPLE 1-2

Production of 5-(benzyloxy)-N-{4-[2-(diethylamino)ethoxy]phenyl}-1H-indole-2-carboxamide The entitled compound was obtained as a white solid in the same manner as in Example 1-1 but using 5-hydroxyindole-2-carboxylic acid and 4-[2-(diethylamino)ethoxy]aniline.

$^1$H-NMR (400 MHz, DMSO-d$_6$, δ ppm): 0.98 (6H, t, J=7.2 Hz), 2.50-2.62 (4H, m), 2.72-2.84 (2H, m), 4.00 (2H, t, J=6.0 Hz), 5.10 (2H, s), 6.91-6.94 (3H, m), 7.21 (1H, J=2.4 Hz), 7.25 (1H, d, J=2.4 Hz), 7.29-7.40 (3H, m), 7.45-7.47 (2H, m), 7.65 (2H, d, J=9.2 Hz), 10.00 (1H, s), 11.52 (1H, s).

ESI-MS Found: m/z 458[M+H]$^+$, 456[M−H]$^-$.

EXAMPLE 1-3

Production of 5-(benzyloxy)-N-{4-[(diethylamino)methyl]phenyl}-1H-indole-2-carboxamide The entitled compound was obtained as a white solid in the same manner as in Example 1-1 but using 5-hydroxyindole-2-carboxylic acid and the compound obtained in Reference Example 2-1-(2).

$^1$H-NMR (400 MHz, DMSO-d$_6$, δ ppm): 1.05 (6H, t, J=6.4 Hz), 2.58-2.72 (4H, m), 3.62-3.84 (2H, m), 5.10 (2H, s), 6.94 (1H, dd, J=9.2, 2.0 Hz), 7.22 (1H, d, J=2.0 Hz), 7.29-7.40 (7H, m), 7.46-7.48 (2H, m), 7.75 (2H, d, J=8.4 Hz), 10.15 (1H, s), 11.57 (1H, s).

ESI-MS Found: m/z 428[M+H]$^+$, 426[M−H]$^-$.

EXAMPLE 1-4

Production of 5-(benzyloxy)-N-{4-[(diethylamino)ethyl]phenyl}-1H-indole-2-carboxamide The entitled compound was obtained as a white solid in the same manner as in Example 1-1 but using 5-hydroxyindole-2-carboxylic acid and the compound obtained in Reference Example 2-4-(3).

¹H-NMR (400 MHz, DMSO-d₆, δ ppm): 1.02 (6H, t, J=6.8 Hz), 2.55-2.78 (8H, m), 5.10 (2H, s), 6.94 (1H, dd, J=9.2, 1.6 Hz), 7.19-7.21 (3H, m), 7.29-7.40 (5H, m), 7.46-7.47 (2H, m), 7.68 (2H, d, J=8.0 Hz), 10.07 (1H, s), 11.55 (1H, s).

ESI-MS Found: m/z 442[M+H]⁺, 420[M−H]⁻.

EXAMPLE 1-5

Production of 5-(benzyloxy)-N-{4-[(diethylamino)methyl]phenyl}-N-methyl-1H-indole-2-carboxamide The entitled compound was obtained as a yellow solid in the same manner as in Example 1-1 but using 5-hydroxyindole-2-carboxylic acid and the compound obtained in Reference Example 2-5-(2).

¹H-NMR (400 MHz, DMSO-d₆, δ ppm): 0.99 (6H, t, J=6.8 Hz), 2.48-2.50 (4H, m), 3.35 (3H, s), 3.58 (2H, brs), 4.96 (2H, s), 5.06 (1H, brs), 6.70 (1H, d, J=2.0 Hz), 6.83 (1H, dd, J=8.8, 2.0 Hz), 7.25-7.28 (4H, m), 7.30-7.39 (6H, m), 11.39 (1H, s).

ESI-MS Found: m/z 442[M+H]⁺, 440[M−H]⁻,

EXAMPLE 1-6

Production of 5-(benzyloxy)-N-{4-[(diethylamino)methyl]phenyl}-1-methyl-1H-indole-2-carboxamide The entitled compound was obtained as a red brown solid in the same manner as in Example 1-1 but using the compound obtained in Reference Example 1-1-(2) and the compound obtained in Reference Example 2-1-(2).

¹H-NMR (400 MHz, DMSO-d₆, δ ppm): 0.99 (6H, t, J=6.8 Hz), 2.44-2.54 (4H, m), 3.52 (2H, brs), 3.96 (3H, s), 5.12 (2H, s), 5.06 (1H, brs), 7.02 (1H, dd, J=9.2, 2.0 Hz), 7.17 (1H, s), 7.22 (1H, d, J=2.8 Hz), 7.26-7.32 (3H, m), 7.35-7.39 (2H, m), 7.45-7.48 (3H, m), 7.69 (2H, d, J=8.0 Hz), 10.19 (1H, s).

ESI-MS Found: m/z 442[M+H]⁺, 440[M−H]⁻.

EXAMPLE 1-7

Production of N-{4-[(diethylamino)methyl]phenyl}-5-(2-pyridinylmethoxy)-1H-indole-2-carboxamide ditrifluoroacetate The entitled compound was obtained as a red brown solid in the same manner as in Example 1-1, for which, however, the compound obtained in Reference Example 1-2-(3) and the compound obtained in Reference Example 2-1-(2) were used and the product was purified through reversed-phase preparative column chromatography.

¹H-NMR (400 MHz, DMSO-d₆, δ ppm): 1.25 (6H, t, 7.2 Hz), 3.00-3.18 (4H, m), 4.29 (2H, d, J=5.5 Hz), 5.25 (2H, s), 7.04 (1H, dd, J=9.0, 2.3 Hz), 7.27 (1H, d, J=2.3 Hz), 7.36 (1H, d, J=1.6 Hz), 7.41 (1H, d, J=9.1 Hz), 7.46-7.52 (1H, m), 7.52 (2H, d, J=8.6 Hz), 7.65 (1H, d, J=8.2 Hz), 7.90 (2H, d, J=8.6 Hz), 7.94-7.96 (1H, m), 8.63-8.67 (1H, m), 10.33 (1H, s), 11.67 (1H, s).

ESI-MS Found: m/z 429[M+H]⁺.

EXAMPLE 1-8

Production of 5-[(6-chloro-3-pyridinyl)methoxy]-N-{4-[(diethylamino)methyl]phenyl}-1H-indole-2-carboxamide trifluoroacetate The entitled compound was obtained as a pale yellow solid in the same manner as in Example 1-1, for which, however, the compound obtained in Reference Example 1-3 and the compound obtained in Reference Example 2-1-(2) were used and the product was purified through reversed-phase preparative column chromatography.

¹H-NMR (400 MHz, DMSO-d₆, δ ppm): 1.23 (6H, t, J=7.2 Hz), 3.06-3.09 (4H, m), 4.27 (2H, d, J=5.1 Hz), 5.17 (2H, s), 6.98 (1H, dd, J=9.0, 2.3 Hz), 7.27 (1H, d, J=2.3 Hz), 7.35-7.38 (2H, m), 7.50 (2H, d, J=8.6 Hz), 7.56 (1H, d, J=8.2 Hz), 7.89 (2H, d, J=8.6 Hz), 7.96 (1H, dd, J=8.2, 2.3 Hz), 8.53 (1H, d, J=2.0 Hz), 10.32 (1H, s), 11.66 (1H, s).

ESI-MS Found: m/z 463[M+H]⁺.

EXAMPLE 1-9

Production of 5-[(5-chloro-3-pyridinyl)methoxy]-N-{4-[(diethylamino)methyl]phenyl}-1H-indole-2-carboxamide The entitled compound was obtained as a pale yellow solid in the same manner as in Example 1-1 but using the compound obtained in Reference Example 1-4 and the compound obtained in Reference Example 2-1-(2).

¹H-NMR (400 MHz, DMSO-d₆, δ ppm): 0.97 (6H, t, J=7.0 Hz), 2.44 (4H, q, J=7.0 Hz), 3.48 (2H, s), 5.19 (2H, s), 6.98 (1H, dd, J=8.8, 2.5 Hz), 7.22 (1H, d, J=2.3 Hz), 7.28 (3H, t, J=7.2 Hz), 7.37 (1H, d, J=9.0 Hz), 7.60 (1H, d, J=8.6 Hz), 7.71 (2H, d, J=8.6 Hz), 7.97 (1H, dd, J=8.4, 2.5 Hz), 8.63-8.64 (1H, m), 10.12 (1H, s), 11.63 (1H, s).

ESI-MS Found: m/z 463[M+H]⁺.

EXAMPLE 1-10

Production of 5-[(5-trifluoromethyl-2-pyridinyl)methoxy]-N-{4-[(diethylamino)methyl]phenyl}-1H-indole-2-carboxamide trifluoroacetate The entitled compound was obtained as a pale yellow solid in the same manner as in Example 1-1, for which, however, the compound obtained in Reference Example 1-5 and the compound obtained in Reference Example 2-1-(2) were used and the product was purified through reversed-phase preparative column chromatography.

¹H-NMR (400 MHz, DMSO-d₆, δ ppm): 1.23 (6H, t, J=7.2 Hz), 3.02-3.11 (4H, m), 4.27 (2H, d, J=5.1 Hz), 5.32 (2H, s), 7.04 (1H, dd, J=9.0, 2.3 Hz), 7.25 (1H, d, J=2.3 Hz), 7.34 (1H, d, J=1.6 Hz), 7.40 (1H, d, J=9.0 Hz), 7.50 (2H, d, J=8.6 Hz), 7.79 (1H, d, J=8.2 Hz), 7.89 (2H, d, J=9.0 Hz), 8.26 (1H, dd, J=8.4, 2.2 Hz), 8.98-9.00 (1H, m), 10.32 (1H, s), 11.67 (1H, d, J=1.6 Hz).

ESI-MS Found: m/z 497[M+H]⁺.

EXAMPLE 1-11

Production of 5-(benzyloxy)-N-[3-methoxy-4-(morpholinomethyl)phenyl]-1H-indole-2-carboxamide The entitled compound was obtained as a pale yellow solid in the same manner as in Example 1-1 but using 5-hydroxyindole-2-carboxylic acid and the compound obtained in Reference Example 2-3-(3).

¹H-NMR (400 MHz, CDCl₃, δ ppm): 2.47-2.62 (4H, m), 3.59 (2H, s), 3.73-3.83 (4H, m), 3.89 (3H, s), 5.13 (2H, s), 7.05-7.11 (3H, m), 7.14-7.22 (1H, m), 7.30-7.44 (5H, m), 7.44-7.51 (2H, m), 7.53-7.57 (1H, m).

ESI-MS Found: m/z 472[M+H]⁺.

EXAMPLE 1-12

Production of 5-(benzyloxy)-N-{6-[[2-(dimethylamino)ethyl](methyl)amino]-3-pyridinyl}-1H-indole-2-carboxamide The entitled compound was obtained as a pale pink solid in the same manner as in Example 1-1 but using 5-hydroxyindole-2-carboxylic acid and the compound obtained in Reference Example 2-6-(2).

$^1$H-NMR (400 MHz, DMSO-$d_6$, δ ppm): 2.17 (6H, s), 2.38 (2H, t, J=7.0 Hz), 2.98 (3H, s), 3.59 (2H, t, J=7.0 Hz), 5.10 (2H, s), 6.61 (1H, d, J=9.0 Hz), 6.93 (1H, dd, J=8.8, 2.5 Hz), 7.21-7.25 (2H, m), 7.32-7.39 (4H, m), 7.45-7.50 (2H, m), 7.81 (1H, dd, J=9.0, 2.7 Hz), 8.38 (1H, d, J=2.3 Hz), 9.98 (1H, s), 11.57 (1H, s).

ESI-MS Found: m/z 444[M+H]$^+$.

EXAMPLE 1-13

Production of 5-(benzyloxy)-N-{6-[isopropyl(methyl)amino]-3-pyridinyl}-1H-indole-2-carboxamide trifluoroacetate The entitled compound was obtained as a pale yellow solid in the same manner as in Example 1-1, for which, however, the 5-hydroxyindole-2-carboxylic acid and the compound obtained in Reference Example 2-7 were used and the product was purified through reversed-phase preparative column chromatography.

$^1$H-NMR (400 MHz, DMSO-$d_6$, δ ppm): 1.19 (6H, d, J=6.7 Hz), 2.93 (3H, s), 4.50-4.52 (1H, m), 5.10 (2H, s), 6.96 (1H, dd, J=8.8, 2.5 Hz), 7.22-7.27 (3H, m), 7.30-7.41 (4H, m), 7.47-7.48 (2H, m), 8.08 (1H, d, J=9.4 Hz), 8.52 (1H, d, J=2.3 Hz), 10.33 (1H, s), 11.67 (1H, s).

ESI-MS Found: m/z 415[M+H]$^+$.

EXAMPLE 1-14

Production of 5-(benzyloxy)-N-[4-(morpholinomethyl)phenyl]-1H-benzimidazole-2-carboxamide The entitled compound was obtained as a colorless solid in the same manner as in Example 1-1 but using the compound obtained in Reference Example 1-6-(4) and the compound obtained in Reference Example 2-2.

$^1$H-NMR (400 MHz, DMSO-$d_6$, δ ppm): 2.31-2.36 (4H, m), 3.42 (2H, s), 3.54-3.58 (4H, m), 5.16 (2H, s), 6.99-7.10 (2H, m), 7.25-7.30 (2H, m), 7.31-7.51 (5H, m), 7.67 (1H, d, J=8.6 Hz), 7.84 (2H, d, J=8.6 Hz), 10.73-10.75 (1H, m), 13.23-13.31 (1H, m)

ESI-MS Found: m/z 443[M+H]$^+$.

REFERENCE EXAMPLE 3-1

Production of 5-(benzyloxy)-N-(4-formylphenyl)-1H-indole-2-carboxamide (1) Diisopropylethylamine (673 μL) was added to a DMF solution (2.0 mL) of 5-hydroxyindole-2-carboxylic acid (516 mg), 4-amino-benzyl alcohol (262 mg) and HATU (734 mg), and stirred at room temperature for 2.5 hours. The reaction liquid was diluted with ethyl acetate, and the organic layer was washed with aqueous saturated sodium hydrogencarbonate solution and saturated saline water. The organic layer was dried with anhydrous magnesium sulfate, and then concentrated under reduced pressure. The residue was diluted with diethyl ether and the resulting crystal was taken out through filtration to obtain 5-(benzyloxy)-N-[4-(hydroxymethyl)phenyl]-1H-indole-2-carboxamide (541 mg) as a brown solid.

ESI-MS Found: m/z 373[M+H]$^+$.

(2) Manganese dioxide (478 mg) was added to an ethyl acetate solution (50 mL) of the obtained compound (205 mg), and stirred at room temperature for 3 hours. The reaction liquid was filtered through Celite, and the filtrate was concentrated under reduced pressure. The residue was washed with diethyl ether to obtain the entitled compound (203 mg) as a brown solid.

ESI-MS Found: m/z 371[M+H]$^+$.

REFERENCE EXAMPLE 3-2

Production of N-(4-acetylphenyl)-5-(benzyloxy)-1H-indole-2-carboxamide

The entitled compound was obtained as a yellow solid in the same manner as in Reference Example 3-1-(1) but using 5-hydroxyindole-2-carboxylic acid and 4-aminoacetophenone.

ESI-MS Found: m/z 371[M+H]$^+$.

REFERENCE EXAMPLE 3-3

Production of 5-(benzyloxy)-N-(5-formyl-2-pyridinyl)-1H-indole-2-carboxamide (1) At 0° C., lithiumaluminium hydride (1.7 g) was added to a THF solution (58 mL) of 6-amino-nicotinic acid (2.0 g), and stirred overnight at room temperature. Sodium sulfate 10 hydrate was added to the reaction liquid at 0° C. to stop the reaction, and this was dried with anhydrous sodium sulfate. The reaction mixture was filtered through Celite, and the filtrate was concentrated under reduced pressure to obtain (6-amino-3-pyridinyl)methanol (1.7 g) as a brown solid.

ESI-MS Found: m/z 125[M+H]$^+$.

(2) At 0° C., tert-butyldimethylsilyl chloride (243 mg) was added to a DMF solution (1.6 mL) of the obtained compound (200 mg) and imidazole (329 mg), and stirred at room temperature for 1 hour. Aqueous sodium hydrogencarbonate solution was added to the reaction liquid to stop the reaction, and this was extracted with diethyl ether. The organic layer was washed with water and saturated saline water, and then dried with anhydrous sodium sulfate. The organic layer was concentrated under reduced pressure, and the residue was purified through thin-layer silica gel chromatography (hexane/ethyl acetate=2/8) to obtain 5-({[tert-butyl(dimethyl)silyl]oxy}methyl)-2-pyridinamine (220 mg) as a white solid.

ESI-MS Found: m/z 239[M+H]$^+$.

(3) At 0° C., 2-chloro-1,3-dimethyl-imidazolinium chloride (53 mg) was added to a chloroform (1.5 mL)/pyridine (1.5 mL) mixed solution of the obtained compound (50 mg) and 5-hydroxyindole-2-carboxylic acid (56 mg), and stirred at room temperature for 3 hours. Further, 2-chloro-1,3-dimethyl-imidazolinium chloride (107 mg) was added to the reaction liquid, and stirred overnight at 50° C. Aqueous sodium hydrogencarbonate solution was added to the reaction liquid to stop the reaction, and this was extracted with chloroform. The organic layer was washed with water and saturated saline water, and then dried with anhydrous sodium sulfate. The organic layer was concentrated under reduced pressure, and the residue was purified through thin-layer silica gel chromatography (hexane/ethyl acetate=2/8) to obtain 5-(benzyloxy)-N-[5-({[tert-butyl(dimethyl)silyl]oxy}methyl)-2-pyridinyl]-1H-indole-2-carboxamide (33 mg) as brown solid.

ESI-MS Found: m/z 488[M+H]$^+$, 486[M–H]$^-$.

(4) At 0° C., a THF solution (205 μL) of 1.0 M tetrabutylammonium fluoride was added to a THF solution (1.5 mL) of the compound (33 mg) obtained in the above, and stirred for 1 hour. Aqueous sodium hydrogencarbonate solution was added to the reaction liquid to stop the reaction, and this was extracted with ethyl acetate. The organic layer was washed with saturated saline water, and then dried with anhydrous sodium sulfate. The organic layer was concentrated under reduced pressure, and the residue was purified through thin-layer silica gel chromatography (chloroform/methanol=9/1) to obtain 5-(benzyloxy)-N-[5-(hydroxymethyl)-2-pyridinyl]-1H-indole-2-carboxamide (19 mg) as an yellow solid.

ESI-MS Found: m/z 374[M+H]$^+$, 372[M–H]$^-$.

(5) The entitled compound was obtained in the same manner as in Reference Example 3-1-(2) but using the compound obtained in the above.

ESI-MS Found: m/z 372[M+H]$^+$, 370[M–H]$^-$.

REFERENCE EXAMPLE 3-4

Production of 5-(benzyloxy)-N-(6-cyano-3-pyridinyl)-1H-indole-2-carboxamide

At 0° C., 2-chloro-1,3-dimethyl-imidazolinium chloride (1.0 g) was added to a chloroform (6.0 mL)/pyridine (6.0 mL) mixed solution of 5-amino-2-cyanopyridine (500 mg) and 5-hydroxyindole-2-carboxylic acid (1.1 g), and stirred for 3 hours, and further stirred overnight at room temperature. Aqueous sodium hydrogencarbonate solution was added to the reaction liquid to stop the reaction, and this was extracted with chloroform. The organic layer was washed with water and saturated saline water, and then dried with anhydrous sodium sulfate. The organic layer was concentrated under reduced pressure, and the resulting crystal was washed with chloroform to obtain the entitled compound (1.4 g) as a pale red solid.

ESI-MS Found: m/z 369[M+H]$^+$, 367[M–H]$^-$.

EXAMPLE 2-1

Production of 5-(benzyloxy)-N-{4-[(4-methoxypiperidino)methyl]phenyl}-1H-indole-2-carboxamide trifluoroacetate At room temperature, a methanol solution (0.5 mL) of 0.3 M sodium cyanotrihydroborate-zinc chloride was added to a THF (1.5 mL)/methanol (1.0 mL) mixed solution of the compound (18 mg) obtained in Reference Example 3-1-(2) and 4-methoxy-piperidine (2 drops, excess), and stirred for 3 days. The reaction liquid was diluted with chloroform, and the organic layer was washed with aqueous 1 N sodium hydroxide solution. The organic layer was dried with anhydrous magnesium sulfate, and then concentrated under reduced pressure. The residue was purified through reversed-phase preparative column chromatography, and concentrated under reduced pressure to obtain the entitled compound (22 mg) as a colorless solid.

1H-NMR (400 MHz, CD$_3$OD, δ ppm): 1.57-1.68 (1H, m), 1.80-1.91 (1H, m), 2.08-2.16 (1H, m), 2.22-2.30 (1H, m), 2.97-3.07 (1H, m), 3.15-3.24 (1H, m), 3.25-3.29 (1H, m), 3.34 (3H, s), 3.47-3.54 (1H, m), 3.57-3.61 (1H, m), 4.24-4.27 (2H, m), 5.08 (2H, s), 7.00 (1H, dd, J=8.8, 2.2 Hz), 7.16 (1H, d, J=2.2 Hz).

ESI-MS Found: m/z 470[M+H]$^+$.

EXAMPLE 2-2

Production of 5-(benzyloxy)-N-{4-[(dimethylamino)methyl]phenyl}-1H-indole-2-carboxamide trifluoroacetate The entitled compound was obtained as a colorless solid in the same manner as in Example 2-1 but using the compound obtained in Reference Example 3-1-(2) and dimethylamine.

$^1$H-NMR (400 MHz, CD$_3$OD, δ ppm): 2.84 (6H, s), 4.26 (2H, s), 5.08 (2H, s), 6.99 (1H, dd, J=8.8, 2.2 Hz), 7.16 (1H, d, J=2.2 Hz), 7.22 (1H, s), 7.25-7.30 (1H, m), 7.32-7.38 (3H, m), 7.42-7.47 (4H, m), 7.86 (2H, d, J=8.1 Hz).

ESI-MS Found: m/z 400[M+H]$^+$.

EXAMPLE 2-3

Production of 5-(benzyloxy)-N-(4-{[isopropyl(methyl)amino]methyl}phenyl)-1H-indole-2-carboxamide trifluoroacetate The entitled compound was obtained as a colorless solid in the same manner as in Example 2-1 but using the compound obtained in Reference Example 3-1-(2) and N-isopropyl-N-methylamine.

$^1$H-NMR (400 MHz, CD$_3$OD, δ ppm): 1.36-1.42 (6H, m), 2.68 (3H, s), 3.56-3.67 (1H, m), 4.06-4.13 (1H, m), 4.33-4.40 (1H, m), 5.07 (2H, s), 6.99 (1H, dd, J=8.8, 2.2 Hz), 7.16 (1H, d, J=2.2 Hz), 7.22 (1H, s), 7.25-7.30 (1H, m), 7.32-7.38 (3H, m), 7.42-7.48 (4H, m), 7.85 (2H, d, J=8.1 Hz).

ESI-MS Found: m/z 428[M+H]$^+$.

EXAMPLE 2-4

Production of 5-(benzyloxy)-N-(4-{[cyclohexyl(methyl)amino]methyl}phenyl)-1H-indole-2-carboxamide trifluoroacetate The entitled compound was obtained as a colorless solid in the same manner as in Example 2-1 but using the compound obtained in Reference Example 3-1-(2) and N-cyclohexyl-N-methylamine.

$^1$H-NMR (400 MHz, CD$_3$OD, δ ppm): 1.16-1.43 (3H, m), 1.50-1.61 (2H, m), 1.67-1.75 (1H, m), 1.88-1.99 (2H, m), 2.02-2.16 (2H, m), 2.68 (3H, s), 3.19-3.28 (1H, m), 4.03-4.08 (1H, m), 4.34-4.40 (1H, m), 5.07 (2H, s), 7.00 (1H, dd, J=8.8, 2.2 Hz), 7.16 (1H, d, J=2.2 Hz), 7.22 (1H, s), 7.25-7.30 (1H, m), 7.32-7.39 (3H, m), 7.42-7.46 (4H, m).

ESI-MS Found: m/z 468[M+H]$^+$.

EXAMPLE 2-5

Production of 5-(benzyloxy)-N-[4-(piperidinomethyl)phenyl]-1H-indole-2-carboxamide trifluoroacetate The entitled compound was obtained as a colorless solid in the same manner as in Example 2-1 but using the compound obtained in Reference Example 3-1-(2) and piperidine.

¹H-NMR (400 MHz, CD₃OD, δ ppm): 1.41-1.55 (1H, m), 1.64-1.86 (3H, m), 1.87-1.97 (2H, m), 2.85-2.96 (2H, m), 3.39-3.47 (2H, m), 4.21 (2H, s), 5.07 (2H, s), 6.99 (1H, dd, J=8.8, 2.2 Hz), 7.16 (1H, d, J=2.2 Hz), 7.22 (1H, s), 7.25-7.30 (1H, m), 7.32-7.39 (3H, m), 7.41-7.47 (4H, m), 7.84 (2H, d, J=8.1 Hz).

ESI-MS Found: m/z 440[M+H]⁺.

EXAMPLE 2-6

Production of 5-(benzyloxy)-N-[4-(1-pyrrolidinylmethyl)phenyl]-1H-indole-2-carboxamide trifluoroacetate The entitled compound was obtained as a colorless solid in the same manner as in Example 2-1 but using the compound obtained in Reference Example 3-1-(2) and pyrrolidine.

¹H-NMR (400 MHz, CD₃OD, δ ppm): 1.92-2.05 (2H, m), 2.10-2.20 (2H, m), 3.09-3.19 (2H, m), 3.42-3.51 (2H, m), 4.30 (2H, s), 5.07 (2H, s), 6.99 (1H, dd, J=8.8, 2.2 Hz), 7.16 (1H, d, J=2.2 Hz), 7.22 (1H, s), 7.25-7.30 (1H, m), 7.32-7.38 (3H, m), 7.42-7.48 (4H, m), 7.84 (2H, d, J=8.1 Hz).

ESI-MS Found: m/z 426[M+H]⁺.

EXAMPLE 2-7

Production of 5-(benzyloxy)-N-{4-[(diisopropylamino)methyl]phenyl}-1H-indole-2-carboxamide trifluoroacetate The entitled compound was obtained as a colorless solid in the same manner as in Example 2-1 but using the compound obtained in Reference Example 3-1-(2) and diisopropylamine.

¹H-NMR (400 MHz, CD₃OD, δ ppm): 1.41 (6H, d, J=6.6 Hz), 1.46 (6H, d, J=6.6 Hz), 3.75-3.83 (2H, m), 4.33 (2H, s), 5.08 (2H, s), 7.00 (1H, dd, J=8.8, 2.2 Hz), 7.16 (1H, d, J=2.2 Hz), 7.22 (1H, s), 7.25-7.31 (1H, m), 7.32-7.39 (3H, m), 7.42-7.51 (4H, m), 7.85 (2H, d, J=8.8 Hz).

ESI-MS Found: m/z 456[M+H]⁺.

EXAMPLE 2-8

Production of 5-(benzyloxy)-N-(4-{[ethyl(2-mehtoxyethyl)amino]methyl}phenyl)-1H-indole-2-carboxamide The entitled compound was obtained as a white solid in the same manner as in Example 2-1 but using the compound obtained in Reference Example 3-1-(2) and N-ethyl-N-(2-methoxyethyl)amine.

¹H-NMR (400 MHz, DMSO-d₆, δ ppm): 0.97 (3H, t, J=7.2 Hz), 2.45-2.51 (2H, m), 2.56 (2H, t, J=6.4 Hz), 3.21 (3H, s), 3.40 (2H, t, J=6.4 Hz), 3.54 (2H, s), 5.10 (2H, s), 6.95 (1H, dd, J=8.8, 2.4 Hz), 7.23 (1H, d, J=2.4 Hz), 7.26-7.41 (5H, m), 7.47-7.49 (2H, m), 7.71 (2H, d, J=8.0 Hz), 10.11 (1H, s), 11.59 (1H, s).

ESI-MS Found: m/z 458[M+H]⁺, 456[M−H]⁻.

EXAMPLE 2-9

Production of 5-(benzyloxy)-N-(4-{[bis-(2-methoxyethyl)amino]methyl}phenyl)-1H-indole-2-carboxamide The entitled compound was obtained as a white solid in the same manner as in Example 2-1 but using the compound obtained in Reference Example 3-1-(2) and N,N-bis(2-methoxyethyl)amine.

¹H-NMR (400 MHz, DMSO-d₆, δ ppm): 2.64 (4H, t, J=6.4 Hz), 3.21 (6H, s), 3.40 (4H, t, J=6.4 Hz), 3.60 (2H, s), 5.10 (2H, s), 6.95 (1H, dd, J=8.8, 2.4 Hz), 7.23 (1H, d, J=2.4 Hz), 7.27-7.41 (5H, m), 7.47-7.49 (2H, m), 7.71 (2H, d, J=8.4 Hz), 10.11 (1H, s), 11.59 (1H, s).

ESI-MS Found: m/z 488[M+H]⁺, 486[M−H]⁻.

EXAMPLE 2-10

Production of 5-(benzyloxy)-N-(4-{[(2-methoxyethyl)(methyl)amino]methyl}phenyl)-1H-indole-2-carboxamide The entitled compound was obtained as a white solid in the same manner as in Example 2-1 but using the compound obtained in Reference Example 3-1-(2) and N-(2-methoxyethyl)ethyl-N-methylamine.

¹H-NMR (400 MHz, DMSO-d₆, δ ppm): 2.14 (3H, s), 3.22 (3H, s), 3.32 (2H, s), 3.43-3.45 (4H, m), 5.10 (2H, s), 6.95 (1H, dd, J=8.8, 2.4 Hz), 7.23-7.41 (8H, m), 7.47-7.49 (2H, m), 7.72 (2H, d, J=8.0 Hz), 10.12 (1H, s), 11.59 (1H, s).

ESI-MS Found: m/z 444[M+H]⁺, 442[M−H]⁻.

EXAMPLE 2-11

Production of 5-(benzyloxy)-N-[4-(1-morpholinoethyl)phenyl]-1H-indole-2-carboxamide The entitled compound was obtained as a white solid in the same manner as in Example 2-1 but using the compound obtained in Reference Example 3-2 and morpholine.

¹H-NMR (400 MHz, DMSO-d₆, δ ppm): 1.28 (3H, t, J=6.8 Hz), 2.24-2.29 (2H, m), 2.34-2.42 (2H, m), 3.31 (1H, q, J=6.8 Hz), 3.54 (4H, t, J=4.8 Hz), 5.10 (2H, s), 6.93 (1H, dd, J=8.8, 2.0 Hz), 7.21-7.33 (5H, m), 7.35-7.39 (3H, m), 7.45-7.47 (2H, m), 7.71 (2H, d, J=8.4 Hz), 10.10 (1H, s), 11.57 (1H, s).

ESI-MS Found: m/z 456[M+H]⁺, 454[M−H]⁻.

EXAMPLE 2-12

Production of 5-(benzyloxy)-N-[5-(morpholinomethyl)-2-pyridinyl]-1H-indole-2-carboxamide The entitled compound was obtained as a white solid in the same manner as in Example 2-1 but using the compound obtained in Reference Example 3-3-(5) and morpholine.

¹H-NMR (400 MHz, DMSO-d₆, δ ppm): 2.34-2.44 (4H, m), 3,46 (2H, s), 3.57 (4H, t, J=4.8 Hz), 5.10 (2H, s), 6.95 (1H, dd, J=8.4, 2.4 Hz), 7.17 (1H, d, J=2.0 Hz), 7.28-7.39 (4H, m), 7.44-7.49 (3H, m), 7.75 (1H, dd, J=8.4, 2.4 Hz), 8.17 (2H, d, J=8.4 Hz), 8.27 (2H, d, J=2.0 Hz), 10.72 (1H, s), 11.61 (1H, s).

ESI-MS Found: m/z 443[M+H]⁺, 441 [M−H]⁻.

EXAMPLE 2-13

Production of 5-(benzyloxy)-N-[6-(morpholinomethyl)-3-pyridinyl]-1H-indole-2-carboxamide At −78° C., a tetrahydrofuran solution (1.7 mL) of 1.0 M diisobutylaluminium hydride was added to a THF solution (6.0 mL) of the compound (200 mg) obtained in Reference Example 3-4, and stirred for 30 minutes. Aqueous acetic acid solution and aqueous saturated Rochelle salt solution were added to the reaction liquid to stop the reaction, and then this was stirred at room temperature for 30 minutes. The reaction liquid was made to have a pH of 9 with aqueous sodium hydrogencarbonate solution added thereto, and then this was extracted with chloroform. The organic layer was washed with water and saturated saline water, and dried with anhydrous sodium sulfate. The organic layer was concentrated under reduced pressure, and the residue was processed in the same manner as in Example 2-1 to obtain the entitled compound (12 mg) as a yellow solid.

$^1$H-NMR (400 MHz, DMSO-$d_6$, δ ppm): 2.40 (4H, t, J=4.4 Hz), 3.55 (2H, s), 3.58 (4H, t, J=4.4 Hz), 5.10 (2H, s), 6.95 (1H, dd, J=8.4, 2.8 Hz), 7.23 (1H, d, J=2.4 Hz), 7.29-7.48 (8H, m), 8.15 (1H, dd, J=8.4, 2.4 Hz), 8.84 (1H, d, J=2.8 Hz), 10.31 (1H, s), 11.63 (1H, s).

ESI-MS Found: m/z 443[M+H]$^+$, 441[M−H]$^−$.

INDUSTRIAL APPLICABILITY

The compounds of formula [I] of the invention have an MCH-1R antagonistic effect and are useful as preventing or treating agents for metabolic disorders such as, for example, obesity, diabetes, hormone disorder, hyperlipidemia, gout, fatty liver, hepatitis, cirrhosis; cardiovascular disorders such as, for example, stenocardia, acute or congestive heart failure, myocardial infarction, coronary atherosclerosis, hypertension, renal diseases, electrolyte abnormality; central nervous system or peripheral nervous system disorders such as, for example, bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders such as respiratory disorders, cancer or pigmentation.

The invention claimed is:

1. A compound of formula I:

[I]

or pharmaceutically acceptable salt thereof,
wherein:
$R^1$ and $R^2$, together with the nitrogen atom to which they bond, form a 3- to 8-membered aliphatic nitrogenous heterocyclic group optionally substituted with $R^6$;
$R^{3a}$ and $R^{3b}$ are independently selected from a hydrogen atom and a $C_{1-6}$ alkyl group optionally substituted with $R^5$;
$R^4$ is a hydrogen atom, a halogen atom, a $C_{1-6}$ alkyl group optionally substituted with $R^5$, or a $C_{1-6}$ alkyloxy group optionally substituted with $R^5$;
each $R^5$ is independently selected from the group consisting of a hydrogen atom, a halogen atom, a cyano group, a hydroxyl group, an amino group, a $C_{1-6}$ alkyl group optionally substituted with a fluorine atom or a hydroxyl group, a mono-$C_{1-6}$ alkylamino group, a di-$C_{1-6}$ alkylamino group, a $C_{1-6}$ alkyloxy group optionally substituted with a fluorine atom, a $C_{1-6}$ alkyloxy-$C_{1-6}$ alkyl group, a $C_{1-6}$ alkyloxycarbonyl group, a $C_{1-6}$ alkyloxycarbonylamino group, a $C_{1-6}$ alkyloxycarbonyl($C_{1-6}$ alkyl)amino group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl($C_{1-6}$ alkyl)amino group, a carbamoyl group, a mono-$C_{1-6}$ alkylcarbamoyl group, a di-$C_{1-6}$ alkylcarbamoyl group, a carbamoylamino group, a mono-$C_{1-6}$ alkylcarbamoylamino group, a di-$C_{1-6}$ alkylcarbamoylamino group, a mono-$C_{1-6}$ alkylcarbamoyl($C_{1-6}$ alkyl)amino group, a di-$C_{1-6}$ alkylcarbamoyl($C_{1-6}$ alkyl)amino group, a carbamoyloxy group, a mono-$C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, a $C_{1-6}$ alkylsulfonyl($C_{1-6}$ alkyl)amino group, a sulfamoyl group, a mono-$C_{1-6}$ alkylsulfamoyl group, a di-$C_{1-6}$ alkylsulfamoyl group, a sulfamoylamino group, a (mono-$C_{1-6}$ alkylsulfamoyl)amino group, a (di-$C_{1-6}$ alkylsulfamoyl)amino group, a mono-$C_{1-6}$ alkylsulfamoyl($C_{1-6}$ alkyl)amino group, a di-$C_{1-6}$ alkylsulfamoyl($C_{1-6}$ alkyl)amino group and a $C_{1-6}$ alkylsulfinyl group;
$R^6$ is selected from $R^5$ and an oxo group;
X is —N— or —C($R^{3C}$)—, and $R^{3C}$ has the same meaning as that of $R^{3a}$;
$Y_1$ is a $C_{1-3}$ alkylene group or an oxy-$C_{2-3}$ alkylene group, and any hydrogen atom in the $C_{1-3}$ alkylene group or the oxy-$C_{2-3}$ alkylene group is optionally substituted with a $C_{1-4}$ alkyl group; or
$Y_2$ is a $C_{1-4}$ alkylene group or an oxy-$C_{1-4}$ alkylene group, and any hydrogen atom in the $C_{1-4}$ alkylene group or the oxy-$C_{1-4}$ alkylene group is optionally substituted with a $C_{1-4}$ alkyl group;
$Ar_1$ is a divalent group, and represents a monocyclic aromatic carbocyclic group optionally substituted with $R^5$;
$Ar_2$ represents a 5- or 6-membered aromatic carbocyclic group optionally substituted with $R^5$.

2. The compound as claimed in claim 1 or a pharmaceutically acceptable salt thereof, wherein the aliphatic nitrogenous heterocyclic group formed by $R^1$ and $R^2$ together with the nitrogen atom to which they bond is selected from the group consisting of a morpholinyl group, a pyrrolidinyl group, a piperidinyl group, a piperazinyl group, a 3-fluoro-1-pyrrolidinyl group, a 3-hydroxy-1-pyrrolidinyl group, a 2-hydroxymethylpyrrolidin-1-yl group, a 3,3-difluoro-1-pyrrolidinyl group, a 2-oxo-1-pyrrolidinyl group, a 3-oxo-1-pyrrolidinyl group, and a 4-methoxy-1-piperidinyl group.

3. The compound according to claim 2 or a pharmaceutically acceptable salt thereof, wherein $R^{3a}$ and $R^{3b}$ are the same or different and represent a hydrogen atom, a methyl group or an ethyl group.

4. The compound according to claim 3 or a pharmaceutically acceptable salt thereof, wherein $R^4$ is a hydrogen atom or a methyl group.

5. The compound according to claim 4 or a pharmaceutically acceptable salt thereof, wherein X is —N—.

6. The compound according to claim 4 or a pharmaceutically acceptable salt thereof, wherein X is —CH—.

7. The compound according to claim 4 or a pharmaceutically acceptable salt thereof, wherein $Y_1$ is —CH$_2$—, —O—CH$_2$CH$_2$— or —OCH$_2$CH$_2$CH$_2$—.

8. The compound according to claim 7 or a pharmaceutically acceptable salt thereof, wherein $Y_2$ is —CH$_2$—O—.

9. The compound according to claim 1 or a pharmaceutically acceptable salt thereof, wherein $Ar_1$ is selected from the group consisting of:

wherein $R^5$ has the same meaning as in claim 1.

10. The compound according to claim 9 or a pharmaceutically acceptable salt thereof, wherein $Ar_2$ is selected from the group consisting of a phenyl group, a 2-fluorophenyl group, a 3-fluorophenyl group, a 4-fluorophenyl group, a 4-chlorophenyl group, a 3,4-difluorophenyl group, a 2,4-difluorophenyl group, a 2-trifluoromethylphenyl group, a 3-trifluoromethylphenyl group, a 4-trifluoromethylphenyl group, a 4-methoxyphenyl group, and a 4-methanesulfonylphenyl group.

11. The compound according to claim 10 or a pharmaceutically acceptable salt thereof, wherein $Ar_2$ is selected from the group consisting of a phenyl group, a 4-fluorophenyl group, a 4-chlorophenyl group, and a 4-trifluoromethylphenyl group.

12. The compound as claimed in claim 1 or a pharmaceutically acceptable salt thereof, wherein the compound of formula I is selected from the following:
- 5-(benzyloxy)-N-[4-(morpholinomethyl)phenyl]-1H-indole-2-carboxamide,
- 5-(benzyloxy)-N-[3-methoxy-4-(morpholinomethyl)phenyl]-1H-indole-2-carboxamide,
- 5-(benzyloxy)-N-{4-[(4-methoxypiperidino)methyl]phenyl}-1H-indole-2-carboxamide,
- 5-(benzyloxy)-N-[4-(piperidinomethyl)phenyl]-1H-indole-2-carboxamide,
- 5-(benzyloxy)-N-[4-(1-pyrrolidinylmethyl)phenyl]-1H-indole-2-carboxamide,
- 5-(benzyloxy)-N-[4-(morpholinomethyl)phenyl]-1H-benzimidazole-2-carboxamide.

13. The compound according to claim 1 or a pharmaceutically acceptable salt thereof, wherein the compound of formula I is selected from: 5-(benzyloxy)-N-[4-(morpholinomethyl)phenyl]-1H-indole-2-carboxamide, 5-(benzyloxy)-N-[4-(morpholinomethyl)phenyl]-1H-benzimidazole-2-carboxamide, and 5-(benzyloxy)-N-[4-(1-pyrrolidinylmethyl)phenyl]-1H-indole-2-carboxamide.

14. A method for producing a compound of formula I according to claim 1 which comprises:
(1) a step of condensing a compound of a formula II:

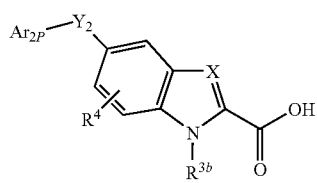

[II]

wherein $Ar_{2P}$ is $Ar_2$, or $Ar_2$ having a protective group; $R^{3b}$, $R^4$, X and $Y_2$ have the same meanings as in claim 1 with a compound of a formula III:

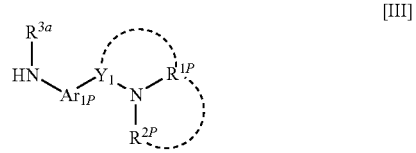

[III]

wherein $R^{1P}$ is $R^1$, or $R^1$ having a protective group; $R^{2P}$ is $R^2$, or $R^2$ having a protective group; $Ar_{1P}$ is $Ar_1$, or $Ar_1$ having a protective group; $R^{3a}$ and $Y_1$ have the same meanings as in claim 1 to give a compound of a formula I-P:

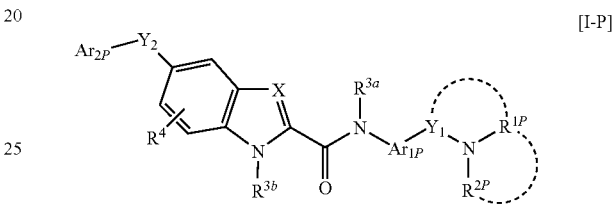

[I-P]

wherein $R^{1P}$, $R^{2P}$, $Ar_{1P}$, $Ar_{2P}$, $R^{3a}$, $R^{3b}$, $R^4$, X, $Y_1$ and $Y_2$ have the same meanings as above, (2) when the compound of formula I-P has a protective group, a step of removing the protective group.

15. A melanin concentrating hormone receptor antagonist comprising a compound according to claim 1 or a pharmaceutically acceptable salt thereof as the active ingredient thereof.

16. A pharmaceutical composition comprising a compound according to claim 1 or a pharmaceutically acceptable salt thereof, and a pharmaceutically-acceptable carrier.

17. The compound according to claim 1 or a pharmaceutically acceptable salt thereof, wherein the compound of formula I is 5-(benzyloxy)-N-[4-(morpholinomethyl)phenyl]-1H-benzimidazole-2-carboxamide.

\* \* \* \* \*